United States Patent [19]
Beavers et al.

[11] Patent Number: 5,580,774
[45] Date of Patent: Dec. 3, 1996

[54] CHIMERIC ANTIBODIES DIRECTED AGAINST A HUMAN GLYCOPROTEIN ANTIGEN

[75] Inventors: Lisa S. Beavers, Trafalgar; Thomas F. Bumol, Carmel; Robert A. Gadski, Indianapolis, all of Ind.

[73] Assignee: Eli Lilly and Company, Indianapolis, Ind.

[21] Appl. No.: 387,665

[22] Filed: Jul. 31, 1989

[51] Int. Cl.⁶ .............................. C12N 5/06; C12N 15/13; C12N 15/85
[52] U.S. Cl. .................................. 435/240.2; 435/320.1; 435/69.6; 536/23.53
[58] Field of Search .............................. 435/320.1, 69.6, 435/240.2; 536/27, 23.53

[56] References Cited

U.S. PATENT DOCUMENTS

| | | | |
|---|---|---|---|
| 4,533,496 | 8/1985 | Lewis et al. | 260/112 |
| 4,816,397 | 3/1989 | Boss et al. | 435/68 |
| 4,816,567 | 3/1989 | Cabilly et al. | 435/68 |
| 5,081,235 | 1/1992 | Shively et al. | 536/25.23 |

OTHER PUBLICATIONS

Schroff et al. Journal of Biological Response Modifiers 6(4) 1987 457–572.
Morgan et al. Cancer Research, 43:3155 1983.
Suggs et al. PNAS. vol. 78. No. 11, pp. 6613–6617 Nov. 1981.
B. Sahagan, et al., *Journal of Immunology*, 137:1066–1074 (1986).
C. Beidler, et al., 053–4060 (1988).
Burstein et al., (1978) *Biochemistry* 17: 2392–2399 and attached computer sheet.
Bumol, T. F. and Reisfeld, R. A. (1982) *Proc. Natl. Acad. Sci.* 79: 1245–1249.
Bumol et al., (1983) *J. Biol. Chem.* 259: 12733–12741.
Yang et al., (1988) *Proc. Natl. Acad. Sci. USA* 85: 1189–1193.
Morrison et al., (1984) *Proc. Natl. Acad. Sci. USA* 81: 6851–6855.

*Primary Examiner*—Lila Feisee
*Attorney, Agent, or Firm*—Douglas K. Norman; Nancy J. Harrison; Paul J. Gaylo

[57] ABSTRACT

The present invention discloses novel chimeric monoclonal antibodies, directed against proteoglycans of human melanoma cells, having antigen-specific variable regions of defined amino acid sequences. DNA constructs for the light and heavy chain variable regions comprising the novel antibodies of the invention are provided. Eukaryotic host cells capable of expression of the chimeric antibodies and comprising the novel chimeric antibody-encoding DNA constructs are also provided.

36 Claims, 12 Drawing Sheets

Restriction Site and Function Map of Plasmid pMLCE-10 pMLCE-10

Restriction Site and Function Map of Plasmid pHKF-1 pHKF-1

Restriction Site and Function Map of Plasmid pHKCE-10

Restriction Site and Function Map of Plasmid pGCEMK pGCEMK

Restriction Site and Function Map of Plasmid pMHCE-30 pMHCE-30

Restriction Site and Function Map of Plasmid pHG1Z pHG1Z

Restriction Site and Function Map of Plasmid pHGCEM-30 pHGCEM-30

Restriction Site and Plasmid Map of Plasmid pNCEMG1 pNCEMG1

Restriction Site and Plasmid Map of Plasmid pTZK910 pTZK910

Restriction Site and Function Map of Plasmid pG9.2.27K pG9.2.27K

Restriction Site and Function Map of Plasmid pG4G21 pG4G21

Restriction Site and Function Map of Plasmid pN9.2.27G1 pN9.2.27G1

CHIMERIC ANTIBODIES DIRECTED AGAINST A HUMAN GLYCOPROTEIN ANTIGEN

SUMMARY OF THE INVENTION

The present invention provides novel DNA compounds and recombinant DNA cloning vectors that encode mouse/human chimeric antibodies derived from monoclonal antibody 9.2.27. The vectors allow expression of the novel DNA compounds in eukaryotic cells. The present invention also provides host cells transformed with these novel cloning vectors. The transformed host cells express the chimeric 9.2.27 antibodies, or derivatives thereof. Many of the present DNA compounds can be used to produce 9.2.27 derivatives never before synthesized either in nature or in the laboratory, and the present invention also comprises these unique molecules.

Monoclonal antibody 9.2.27 is a murine antibody which specifically binds to the ~250,000 dalton glycoprotein which serves as the core protein for Chondroitin Sulfate Proteoglycan found in high density on melanoma cells and found also on several normal tissues including vascular smooth muscle cells. This antibody is useful for the in vitro detection of disease, as well as the in vivo diagnosis and treatment of melanoma. One problem with the use of murine antibodies in human subjects arises when the cancer patient's immune system creates antibodies against the murine immunoglobulins. This immune response does not occur in all patients, but when it does, it results in a gradual decline in the efficacy of treatment during multiple dose regimens. The patient's immune response can cause a rapid clearance of the murine antibody from the patient's bloodstream. Such a response could also lead to more severe reactions like anaphylaxis or serum sickness. This immunogenicity precludes multiple dose administration of the antibody and therefore decreases the clinical value of the treatment.

Human monoclonal antibodies are difficult to prepare, therefore chimeric antibodies are constructed to avoid immunological problems. Chimeric antibodies comprise an antigen specific or variable region derived from one species joined with the constant region from a different species. See, Oi and Morrison, BioTechniques 4:214–221 (1986). Inasmuch as the immune response is often directed against the constant region, the replacement of a murine constant region with a human constant region will greatly diminish a patient's immunological reaction. Accordingly, chimeric antibodies are highly desirable for the treatment of disease.

The general concept of chimeric antibodies has been described, yet the development of novel chimeric antibodies having certain specificities is still needed. The present invention discloses recombinant DNA and amino acid sequences which comprise the variable regions of the 9.2.27 monoclonal antibody molecule. These sequences have been manipulated to express chimeric antibodies which have the same tissue specificity as 9.2.27, but which comprise constant regions derived from human sources. The invention therefore will allow a therapeutic regimen with the same tissue specificity of monoclonal antibody 9.2.27 but with greatly reduced immunological side effects.

For purposes of the present invention, as disclosed and claimed herein, the following terms are as defined below.

A—deoxyadenosine.

Ala—an alanine residue.

$Ap^R$—the ampicillin-resistant phenotype or gene conferring same.

Arg—an arginine residue.

Asn—an asparagine residue.

Asp—an aspartic acid residue.

C—deoxycytosine.

Chimeric antibody—an antibody comprising a variable region from one species, typically mouse, joined to a constant region from a second and different species, typically human.

CSP—Chondroitin Sulfate Proteoglycan.

Cys—a cysteine residue.

dhfr—the dihydrofolate reductase phenotype or gene conferring same.

G—deoxyguanosine.

Gln—a glutamine residue.

Glu—a glutamic acid residue.

Gly—a glycine residue.

$G418^R$—the G418-resistant phenotype or gene conferring same. May also be identified as $Km^R$.

His—a histidine residue.

$Hm^R$—the hygromycin-resistant phenotype or gene conferring same.

Ile—an isoleucine residue.

IVS—DNA encoding an intron, also called an intervening sequence.

Leu—a leucine residue.

Lys—a lysine residue.

Met—a methionine residue.

MoAB—monoclonal antibody.

9.2.27 antigen—the approximately 250,000 dalton glycoprotein which is the core glycoprotein of Chondroitin Sulfate Proteoglycan found on the M21 human melanoma cell line as well as other human melanoma cell lines and human melanoma tumor tissue.

9.2.27—a murine monoclonal antibody derived from a hybridoma cell line, said antibody recognizing the approximately 250,000 dalton glycoprotein which is the core glycoprotein of Chondroitin Sulfate Proteoglycan found on the M21 human melanoma cell line.

Nascent protein—the polypeptide produced upon translation of a mRNA transcript, prior to any post-translational modifications.

Phe—a phenylalanine residue.

Pro—a proline residue.

Promoter—a DNA sequence that directs transcription of DNA into RNA.

Recombinant DNA Cloning Vector—any autonomously replicating agent, including, but not limited to, plasmids and phages, comprising a DNA molecule to which one or more additional DNA segments can be or have been added.

Recombinant DNA Expression Vector—any recombinant DNA cloning vector into which a promoter has been incorporated.

Replicon—A DNA sequence that controls and allows for autonomous replication of a plasmid or other vector.

Restriction Fragment—any linear DNA sequence generated by the action of one or more restriction endonuclease enzymes.

Sensitive Host Cell—a host cell that cannot grow in the presence of a given antibiotic or other toxic compound without a DNA segment that confers resistance thereto.

Ser—a serine residue.

Structural Gene—any DNA sequence that encodes a functional polypeptide, inclusive of translational start and stop signals.

T—deoxythymidine.

Tc$^R$—the tetracycline-resistant phenotype or gene conferring same.

Thr—a threonine residue.

Trp—a tryptophane residue.

Tyr—a tyrosine residue.

Val—a valine residue.

DETAILED DESCRIPTION OF THE INVENTION

Figure 1:
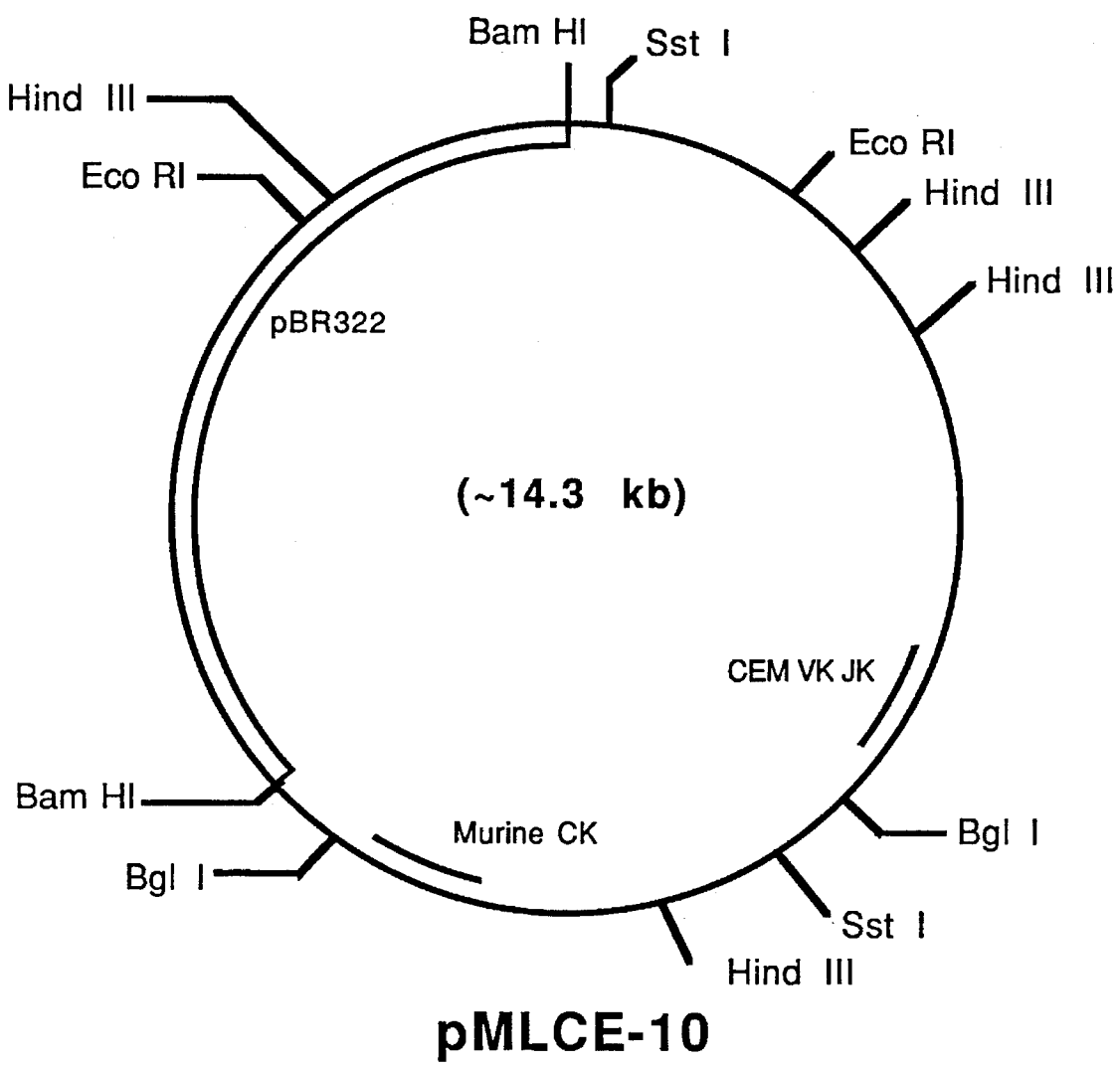
FIG. 1—The Restriction Site and Function Map of Plasmid pMLCE-10. For purposes of the present application, FIG. 1 and all subsequent figures are not drawn precisely to scale.

The present invention is a recombinant DNA compound which comprises DNA encoding a chimeric antibody light chain comprising an antigen-specific variable region derived from a first mammalian species and a constant region derived from a second and different mammalian species, said light chain variable region having an amino acid sequence comprising:

---
Asn—Ile—Val—Leu—Thr—Gln—Ser—Pro—Ala—Ser
Leu—Ala—Val—Ser—Leu—Gly—Gln—Arg—Ala—Thr
Ile—Ser—Cys—Arg—Ala—Ser—Glu—Ser—Val—Asp
Ser—Tyr—Gly—Asn—Ser—Phe—Met—His—Trp—Tyr
Gln—Gln—Lys—Pro—Gly—Gln—Pro—Pro—Lys—Leu
Leu—Ile—Tyr—Leu—Ala—Ser—Asn—Leu—Glu—Ser
Gly—Val—Pro—Ala—Arg—Phe—Ser—Gly—Ser—Gly
Ser—Arg—Thr—Asp—Phe—Thr—Leu—Thr—Ile—Asp
Pro—Val—Glu—Ala—Asp—Asp—Ala—Ala—Thr—Tyr
Tyr—Cys—Gln—Gln—Asn—Asn—Glu—Asp—Pro—Leu
Thr—Phe—Gly—Ser—Gly—Thr—Lys—Leu—Glu—Ile
Lys—Arg.
---

Due to the complementary nature of DNA base pairing, the sequence of one strand of a double-stranded DNA molecule is sufficient to determine the sequence of the opposing strand. The nucleotide sequence of the light chain variable region of monoclonal antibody 9.2.27 is:

---
AAC—ATT—GTG—CTG—ACC—CAA—TCT—CCA—GCT—TCT
TTC—GCT—GTG—TCT—CTA—GGG—CAG—AGG—GCC—ACC
ATA—TCC—TGC—AGA—GCC—AGT—GAA—AGT—GTT—GAT
AGT—TAT—GGC—AAT—AGT—TTT—ATG—CAC—TGG—TAC
CAG—GAG—AAA—CCA—GGA—CAG—CCA—CCC—AAA—CTC
CTC—ATC—TAT—CTT—GCA—TCC—AAC—CTA—GAA—TCT
GGG—GTC—CCT—GCC—AGG—TTC—AGT—GGC—AGT—GGA
TCT—AGG—ACA—GAC—TTC—ACC—CTC—ACC—ATT—GAT
CCT—GTG—GAG—GCT—GAT—GAT—GCT—GCA—ACC—TAT
TAC—TGT—CAA—CAA—AAT—AAT—GAG—GAT—CCT—CTC
ACG—TTC—GGC—TCG—GGG—ACA—AAG—TTG—GAA—ATA
AAA—CGG.
---

Furthermore, the invention also comprises a recombinant DNA compound which comprises DNA encoding a chimeric antibody heavy chain variable region derived from a first mammalian species and a constant region derived from a second and different mammalian species, said heavy chain variable region having an amino acid sequence comprising:

---
Gln—Val—Gln—Leu—Gln—Gln—Ser—Gly—Pro—Glu
Leu—Val—Lys—Pro—Gly—Ala—Ser—Val—Lys—Ile
Ser—Cys—Lys—Ala—Ser—Gly—Tyr—Ala—Phe—Ser
Arg—Ser—Trp—Met—Asn—Trp—Val—Lys—Gln—Arg
Pro—Gly—Gln—Gly—Leu—Glu—Trp—Ile—Gly—Arg
Ile—Tyr—Pro—Gly—Asp—Gly—Asp—Thr—Asn—Tyr
Asn—Gly—Lys—Phe—Lys—Gly—Lys—Ala—Thr—Leu
Thr—Ala—Asp—Lys—Ser—Ser—Ser—Thr—Ala—Tyr
Met—Gln—Val—Ser—Ser—Leu—Thr—Ser—Val—Asp
Ser—Ala—Val—Tyr—Phe—Cys—Ala—Arg—Gly—Asn
Thr—Val—Val—Val—Pro—Tyr—Thr—Met—Asp—Tyr
Trp—Gly—Gln—Gly—Thr—Ser—Val—Thr—Val—Ser
Ser.
---

The nucleotide sequence of the heavy chain variable region of monoclonal antibody 9.2.27 is:

---
CAG—GTC—CAG—CTG—CAG—CAG—TCT—GGA—CCT—GAG
CTG—GTG—AAG—CCT—GGG—GCC—TCA—GTG—AAG—ATT
TCC—TGC—AAA—GCT—TCT—GGC—TAC—GCA—TTC—AGT
AGG—TCT—TGG—ATG—AAC—TGG—GTG—AAG—CAG—AGG
CCT—GGA—CAG—GGT—CTT—GAG—TGG—ATT—GGA—CGG
ATT—TAT—CCT—GGA—GAT—GGA—GAT—ACT—AAC—TAC
AAT—GGG—AAG—TTC—AAG—GGC—AAG—GCC—ACA—CTG
---

```
ACT—GCA—GAC—AAA—TCC—TCC—AGC—ACA—GCC—TAC
ATG—CAG—GTC—AGC—AGC—CTG—ACC—TCT—GTG—GAC
TCT—GCG—GTC—TAT—TTC—TGT—GCA—AGA—GGG—AAT
ACG—GTA—GTA—GTT—CCC—TAT—ACT—ATG—GAC—TAC
TGG—GGT—CAA—GGA—ACC—TCA—GTC—ACC—GTC—TCC
TCA.
```

Both the light chain and heavy chain molecules of the present invention are associated with distinct signal peptides. The amino acid sequence of the light chain signal peptide is:

```
Met—Glu—Thr—Asp—Thr—Leu—Leu—Leu—Trp—Val
Leu—Leu—Leu—Trp—Val—Pro—Gly—Ser—Thr—Gly.
```

The nucleotide sequence of this light chain signal peptide gene is:

```
ATG—GAG—ACA—GAC—ACA—CTC—CTG—CTA—TGG—GTG
CTG—CTG—CTC—TGG—GTT—CCA—GGT—TCC—ACA—GGT.
```

The amino acid sequence of the heavy chain signal peptide is:

```
Met—Gly—Trp—Ser—Arg—Ile—Phe—Leu—Phe—Leu
Leu—Ser—Ile—Thr—Ala—Gly—Val—His—Cys.
```

The nucleotide sequence of this heavy chain signal peptide gene is:

```
ATG—GGA—TGG—AGC—CGG—ATC—TTT—CTC—TTC—CTC
CTG—TCA—ATA—ACT—GCA—GGT—GTC—CAT—TGC.
```

The novel DNA compounds of the present invention are derived from cDNA clones prepared from the mRNA from the hybridoma cell line which makes monoclonal antibody 9.2.27. Plasmid pTZK910 comprises the entire coding sequence of the light chain of monoclonal antibody 9.2.27, the coding sequence of the signal peptide associated with the light chain, and the 5' and 3' untranslated regions of this molecule. The 5' untranslated region has the DNA sequence:

5'-AGTTCCAGGACAGCTAGGGCTATACAGAGAAACCCTGTCTCGAAAAACCAAAAA
AAAAAAAAAACCAGCTCTCAGAG-3'.

Figure 9:
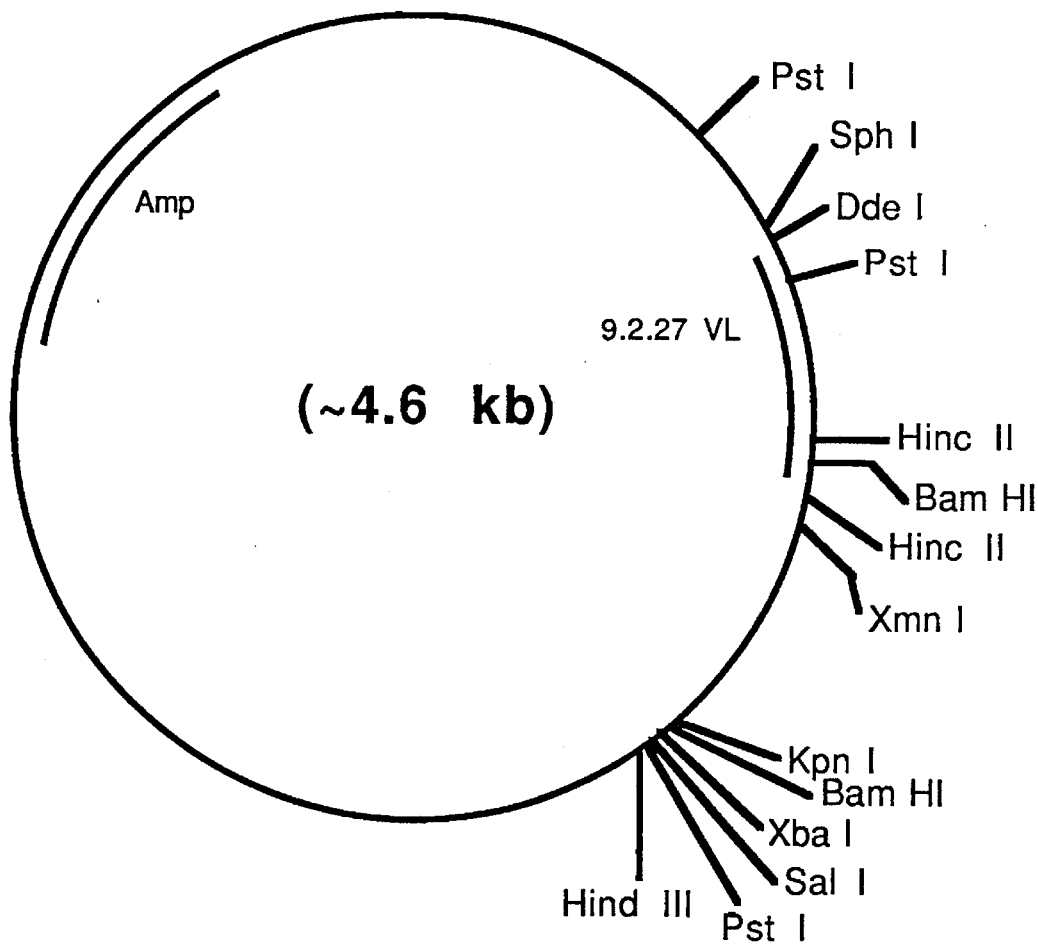
FIG. 9—The Restriction Site and Function Map of Plasmid pTKZK910.

Plasmid pTZK910 can be conventionally isolated from *E. coli* K12 JM109/pTZK910, a strain deposited on Apr. 7, 1989 and made part of the permanent stock culture collection of the Northern Regional Research Laboratory (NRRL), Peoria, Ill., A culture of *E. coli* K12 JM109/pTZK910 can be obtained from the NRRL under the accession number NRRL B-18478. A restriction site and function map of plasmid pTZK910 is presented in FIG. 9 of the accompanying drawings.

Plasmid pG4G21 comprises the entire coding sequence of the heavy chain of monoclonal antibody 9.2.27, the coding sequence of the signal peptide associated with the heavy chain, and the 5' and 3' untranslated regions of this molecule. The 5' untranslated region has the DNA sequence:

5'-TCCTCTACACAGTCCCTGACGACACTGACTCTAACC-3'.

Figure 11:
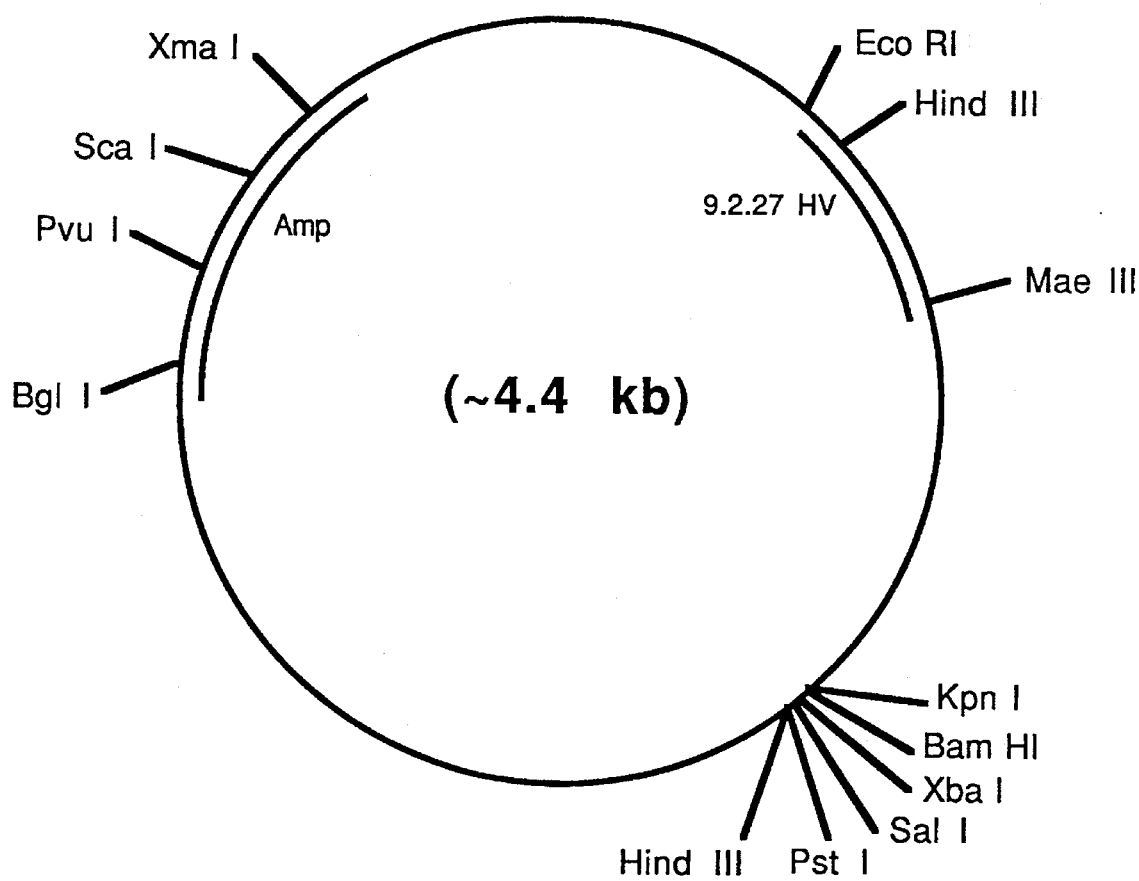
FIG. 11—The Restriction Site and Function Map of Plasmid pG4G21.

Plasmid pG4G21 can be conventionally isolated from *E. coli* K12 DH5/pG4G21, also deposited on Apr. 7, 1989 and made part of the permanent stock culture collection of the NNRL. A culture of *E. coli* K12 DH5/pG4G21 can be obtained from the NRRL under the accession number NRRL B-18479. A restriction site and function map of plasmid pG4G21 is presented in FIG. 11 of the accompanying drawings.

To create a vector for the eukaryotic expression of the 9.2.27 chimeric light chain, it is necessary to insert the gene encoding the 9.2.27 light chain variable region into a vector which contains an efficient eukaryotic promoter and a gene encoding a human light chain constant region. Plasmid pGCEMK comprises a gene encoding a murine variable region which recognizes human carcinoembryonic antigen (CEA) joined to an efficient promoter and a human light chain constant region gene. Replacement of the light chain variable region gene of plasmid pGCEMK with the light chain variable region gene of monoclonal antibody 9.2.27 yields expression vector pG9.2.27K. Plasmid pGCEMK was constructed from plasmids pMLCE-10, pHKF-1 and pSV2-gpt as described in Beidler et al., Chimeric Antibodies Directed Against Human Carcinoembryonic Antigen, U.S. patent application No. 07/272,856, filed Nov. 17, 1988, the entire teaching of which is herein incorporated by reference.

Figure 2:
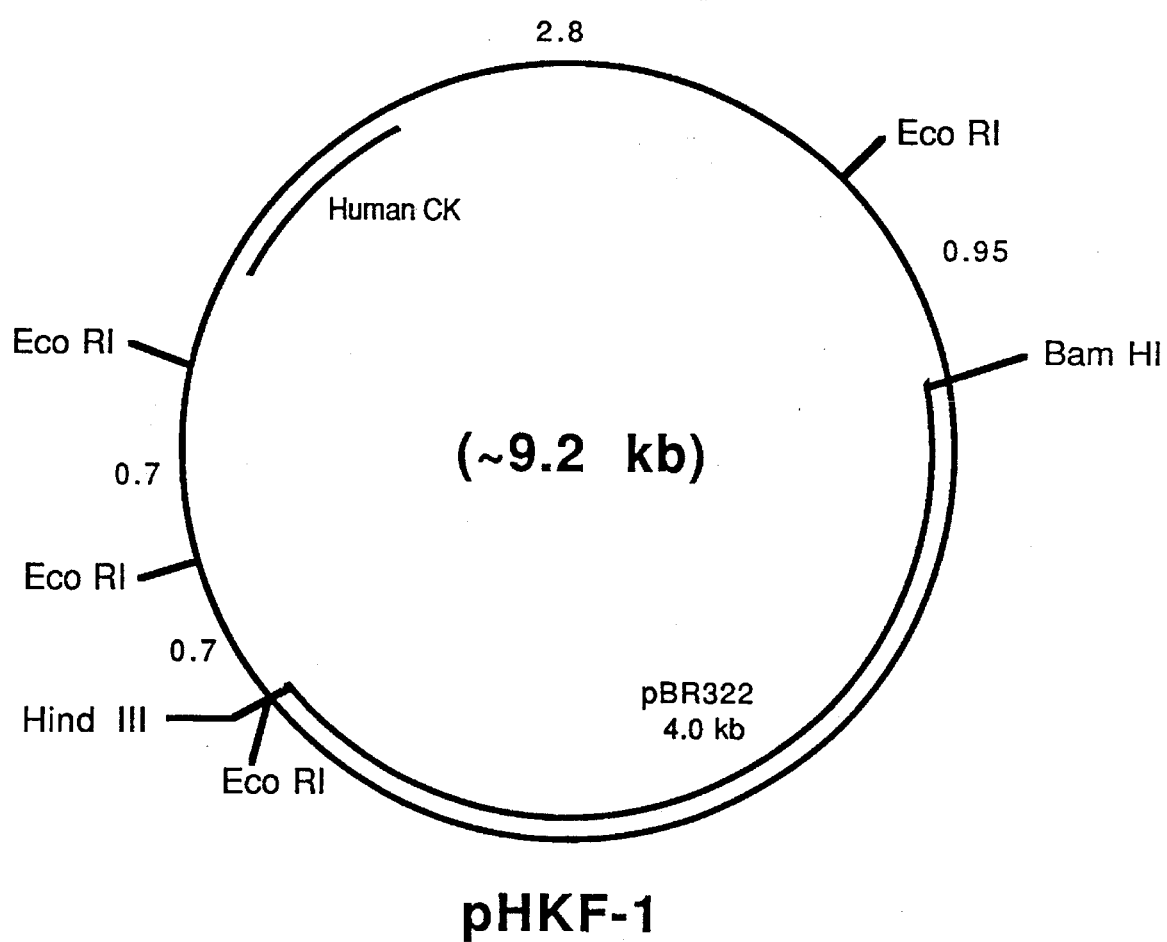
FIG. 2—The Restriction Site and Function Map of Plasmid pHKF-1.

Plasmid pMLCE-10 comprises the genomic sequence of the light chain variable region of monoclonal antibody CEM, which recognizes human carcinoembryonic antigen. Plasmid pMLCE-10 was made part of the permanent collection of the American Type Culture Collection on Mar. 1, 1988 and is available under accession number ATCC 67639. Plasmid pHKF-1 comprises the genomic sequence of the light chain constant region of human antibody. Plasmid pHKF-1 was made part of the ATCC permanent collection on Mar. 1, 1988 and is available under accession number ATCC 67637. Restriction site and function map of plasmids pMLCE-10 and pHKF-1 are presented in FIGS. 1 and 2 of the accompanying drawings, respectively.

Figure 3:
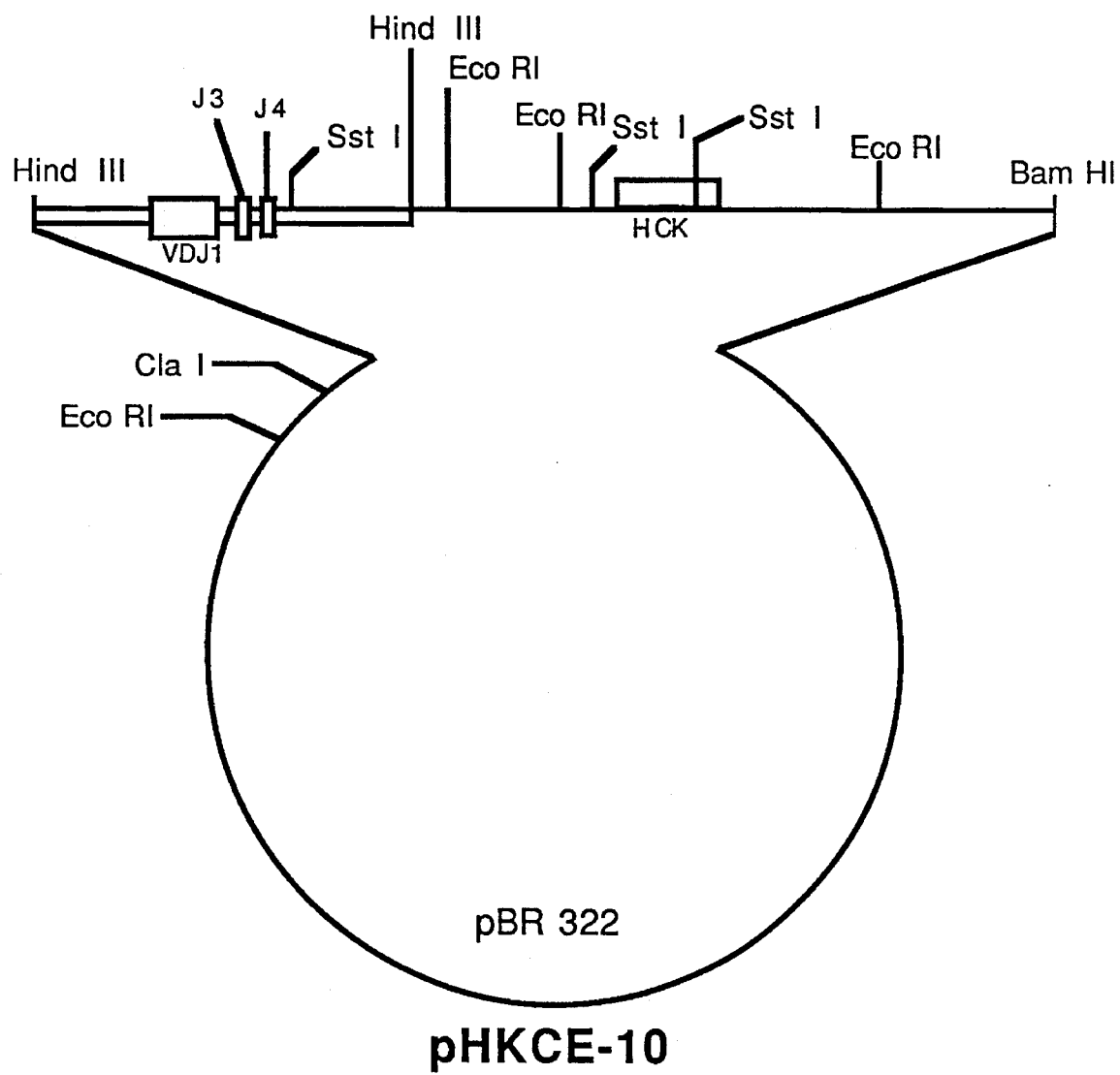
FIG. 3—The Restriction Site and Function Map of Plasmid pHKCE-10.
Figure 4:
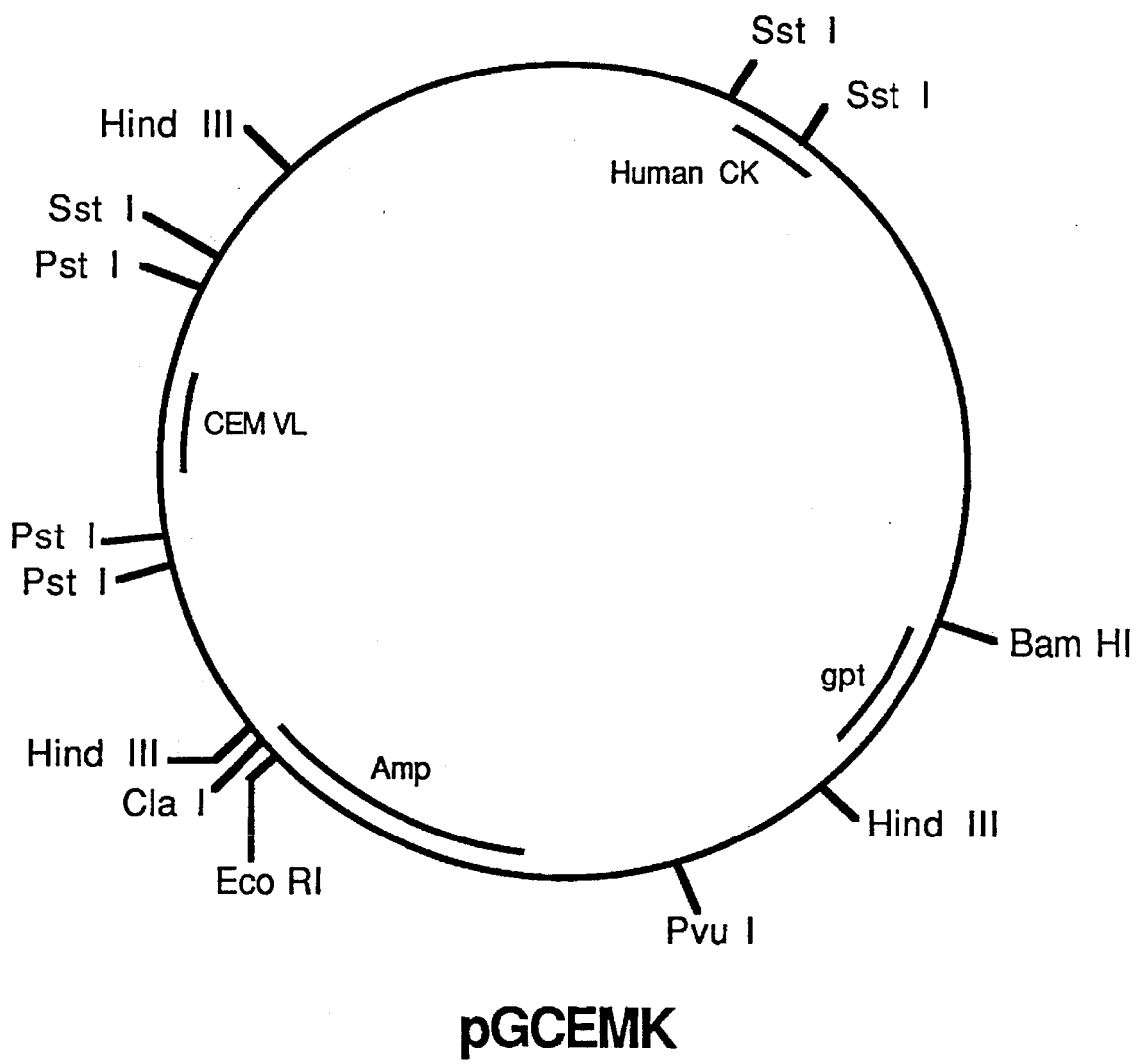
FIG. 4—The Restriction Site and Function Map of Plasmid pGCEMK.

Plasmid pHKCE-10 was constructed by isolating the approximately 3.8 kb HindIII fragment containing the CEM light chain variable region gene from plasmid pMLCE-10 and ligating this fragment into HindIII digested plasmid pHKF-1. Plasmid pSV2gpt (available from the ATCC under accession number ATCC 37145) was digested with restriction enzyme EcpRI and ClaI linkers (sequence dCATC-CGATG) were ligated into the EcoRI site to form plasmid pSV2gpt-Cla. Plasmid pHKCE-10 was next digested with restriction enzymes ClaI and BamHI and the approximately 9.0 kb ClaI/BamHI restriction fragment, which comprises the CEM light chain variable region gene linked to the human light chain constant region gene, was isolated. Plasmid pSV2gpt-Cla was also digested with restriction enzymes ClaI and BamHI and the approximately 4.5 kb ClaI/BamHI restriction fragment was isolated. The about 9.0 kb fragment from plasmid pHKCE-10 was ligated into the about 4.5 kb vector fragment of plasmid pSV2gpt-Cla to form expression plasmid pGCEMK. Restriction site and function maps of plasmids pHKCE-10 and pGCEMK are presented in FIGS. 3 and 4 of the accompanying drawings, respectively.

Plasmid pTZK910 is then digested with restriction enzymes DdeI and BamHI and the approximately 357 base pair DdeI/BamHI restriction fragment, which comprises most of the gene encoding the 9.2.27 kappa variable region, is isolated. A BglII-DdeI linker is then synthesized with the following sequence:

A BamHI-SstII linker, which contains the coding sequence for the 15 amino acids at the NH$_2$ terminus of the 9.2.27 kappa variable region plus a eukaryotic splice site, is then synthesized. This linker has the sequence:

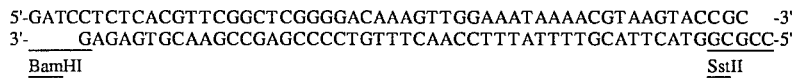

Figure 10:
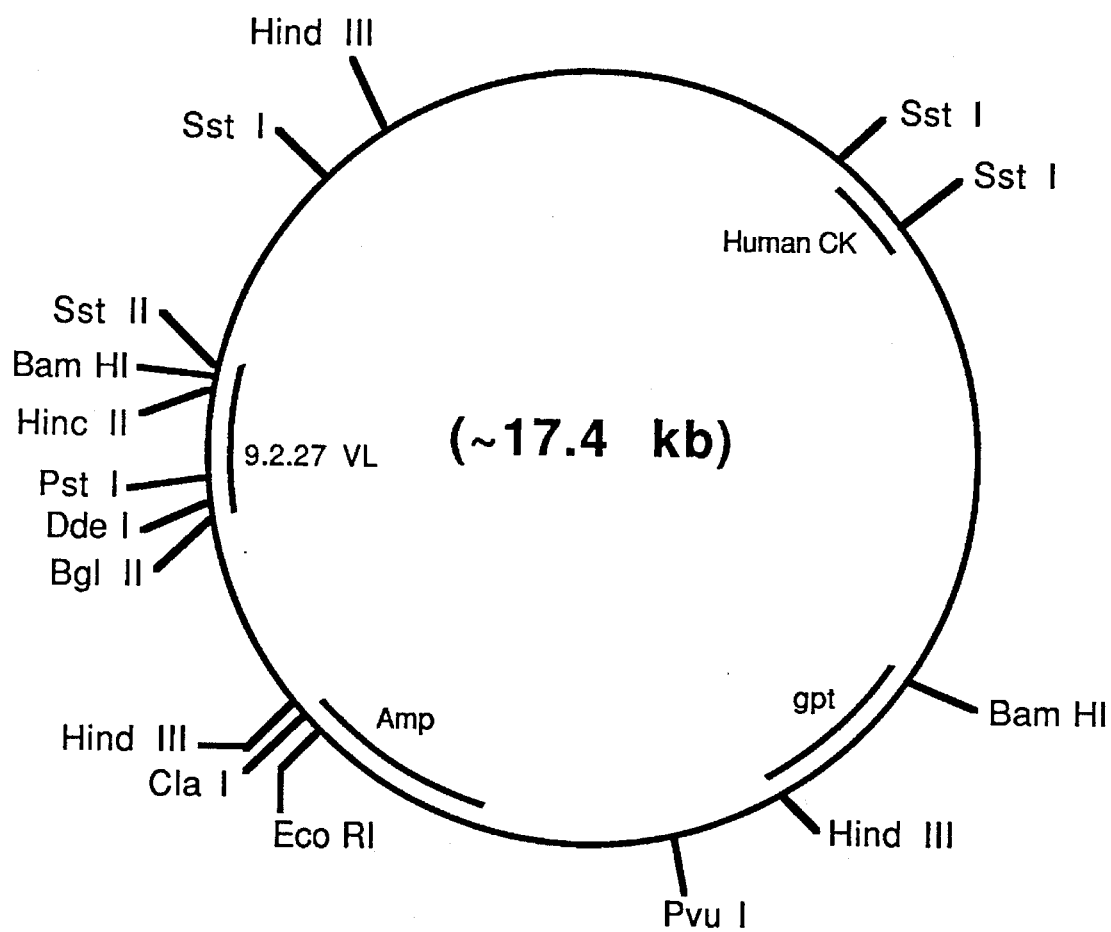
FIG. 10—The Restriction Site and Function Map of Plasmid pG9.2.27K.

The two linkers are next ligated to the approximately 357 bp DdeI/BamHI restriction fragment of plasmid pTZK910. After digestion with restriction enzymes BglII and SstII, this approximately 420 bp fragment is isolated and purified. Plasmid pGCEMK is digested with restriction enzymes BglII and SstII to remove the gene encoding the anti-CEA light chain variable region. The approximately 420 bp BglII/SstII restriction fragment of plasmid pTZK910 is then ligated into the BglII/SstII-digested large vector fragment of plasmid pGCEMK to form plasmid pG9.2.27K, which comprises the kappa promoter of plasmid pGCEMK, the gene encoding the light chain variable region of antibody 9.2.27, a gene encoding a human kappa chain constant region and a gpt resistance conferring gene. A restriction site and function map of plasmid pG9.2.27K is presented in FIG. 10 of the accompanying drawings.

In an analogous manner, a vector for eukaryotic expression of the 9.2.27 heavy chain variable region is created by inserting the 9.2.27 heavy chain variable region gene into a vector which contains a eukaryotic promoter and a gene encoding a human heavy chain (gamma 1) constant region. Plasmid pNCEMG1 comprises a gene encoding a murine variable region which recognizes human CEA joined to a eukaryotic promoter and a human heavy chain constant region gene. Replacement of the heavy chain variable gene of plasmid pNCEMG1 with the heavy chain variable region gene of antibody 9.2.27 yields expression vector pN9.2.27G1. Plasmid pNCEMG1 was constructed from plasmids pMHCE-30, pHG1Z and pSV2neo as described in Beidler et al., U.S. patent application No. 07/272,856, filed Nov. 17, 1988, the entire teaching of which is herein incorporated by reference.

Figure 5:
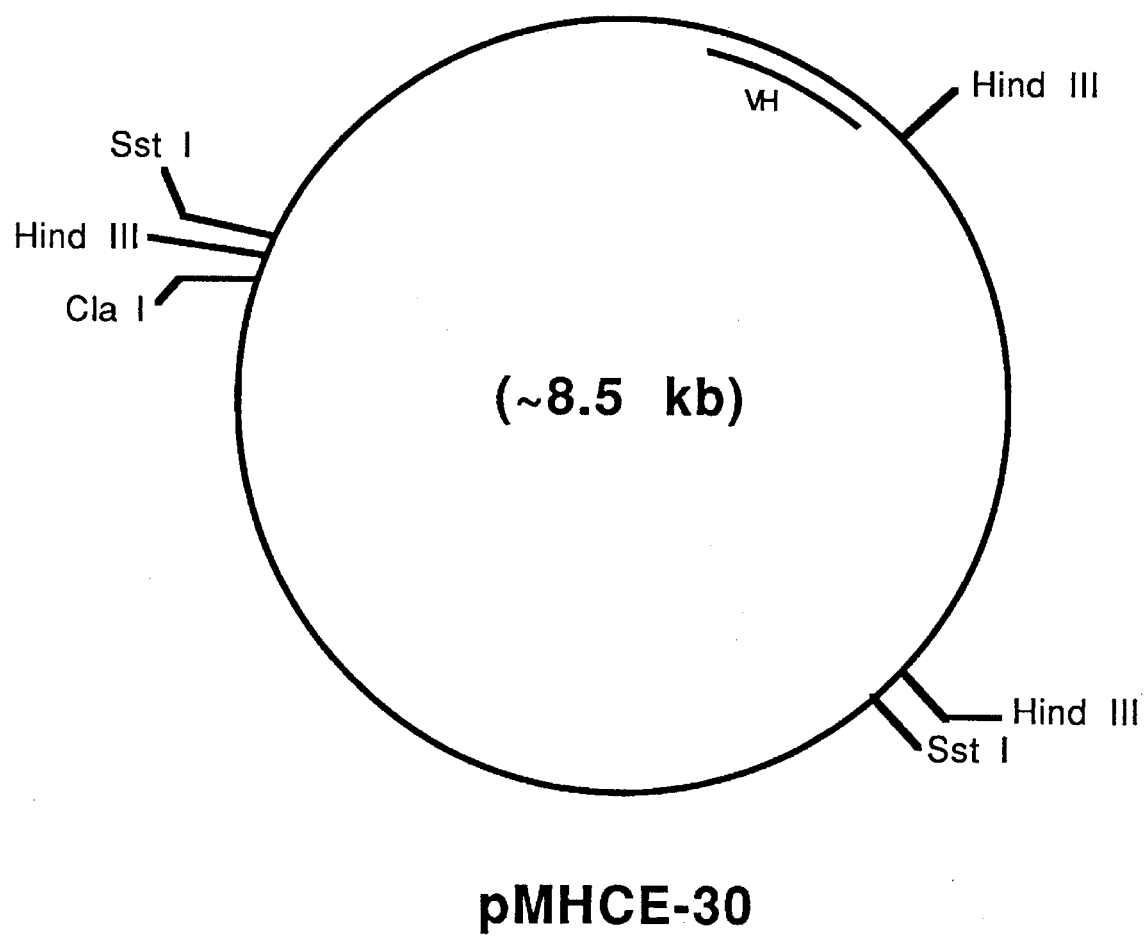
FIG. 5—The Restriction Site and Function Map of Plasmid pMHCE-30.
Figure 6:
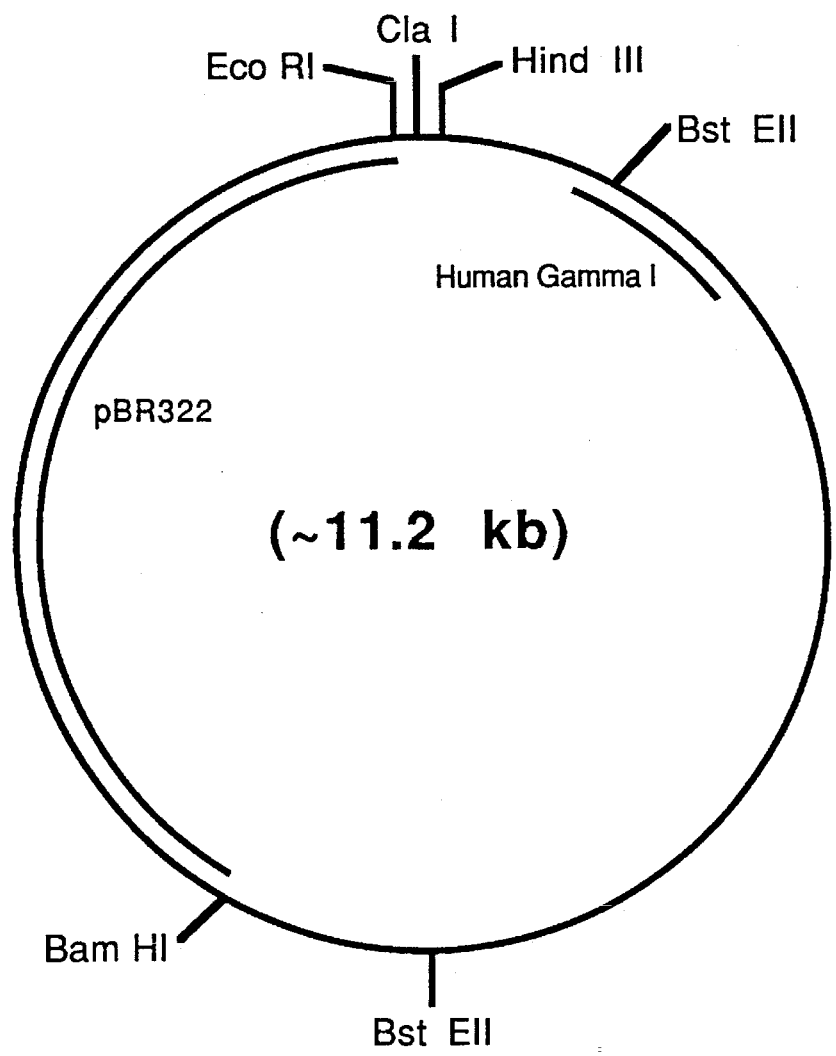
FIG. 6—The Restriction Site and Function Map of Plasmid pHG1Z.

Plasmid pMHCE-30 comprises the genomic sequence of the heavy chain variable region of monoclonal antibody CEM, which recognizes human carcinoembryonic antigen. Plasmid pMHCE-30 was made part of the ATCC collection on Mar. 1, 1988 and is available under accession number ATCC 67640. Plasmid pHG1Z comprises the genomic sequence of the heavy chain variable region of human antibody. Plasmid pHG1Z was deposited with the ATCC on Mar. 1, 1988 and is available under accession number ATCC 67638. Restriction site and function maps of plasmid pMHCE-30 and pHG1Z are presented in FIGS. 5 and 6 of the accompanying drawings, respectively.

Figure 7:
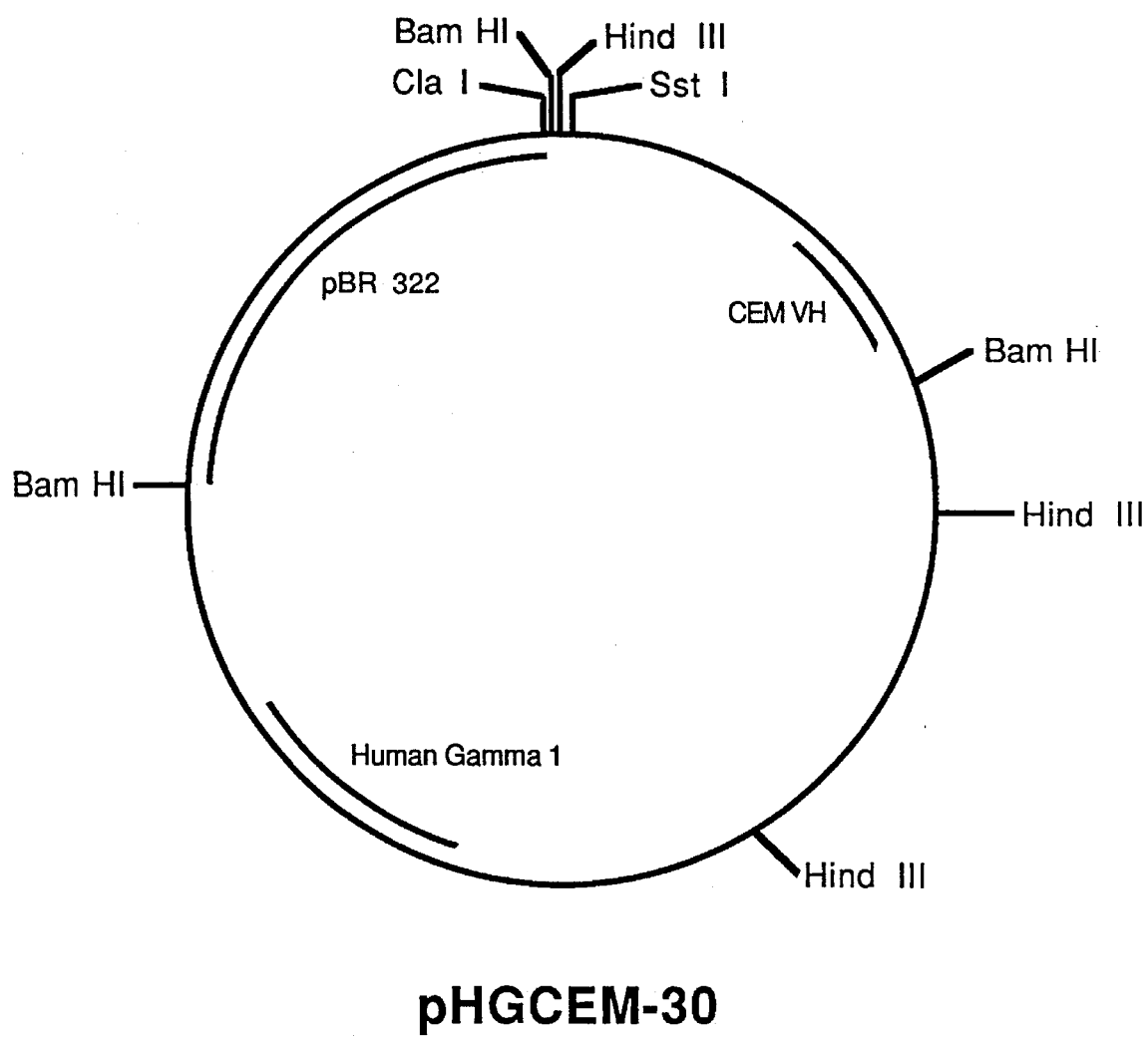
FIG. 7—The Restriction Site and Function Map of Plasmid pHGCEM-30.
Figure 8:
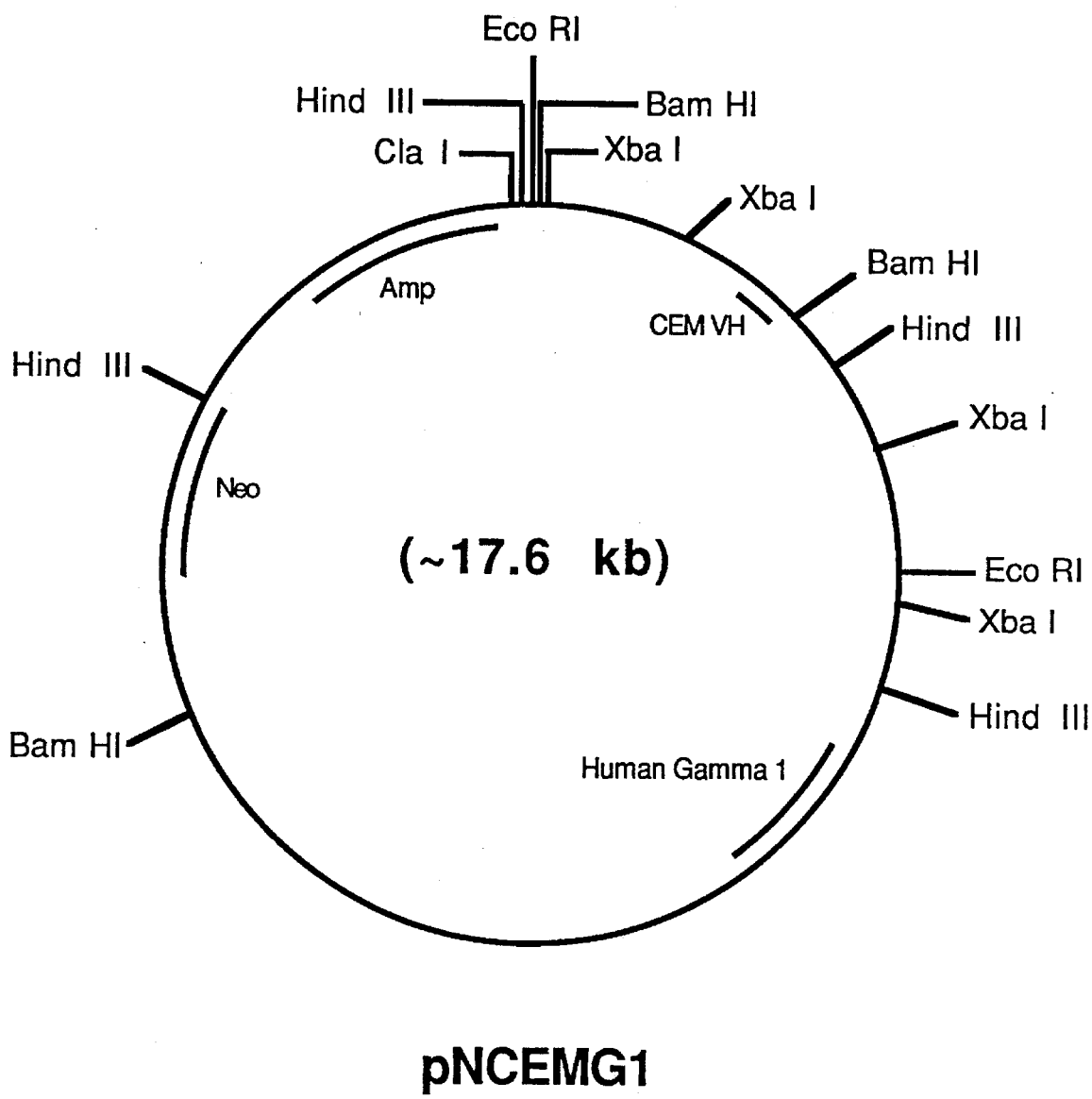
FIG. 8—The Restriction Site and Function Map of Plasmid pNCEMG1.

Plasmid pHGCEM-30 was constructed by isolating the approximately 5.3 kb ClaI/HindIII fragment containing the CEM heavy chain variable region gene from plasmid pMHCE-30 and ligating this fragment into ClaI/HindIII digested vector pHG1Z. Inasmuch as plasmid pMHCE-30 contains more than one BamHI site, the 5.3 kb ClaI/HindIII restriction fragment of plasmid pMHCE-30 is most easily isolated following a total ClaI digested and a subsequent partial BamHI digestion. Plasmid pSV2neo (ATCC 37149) was digested with restriction enzyme EcoRI and ClaI linkers (dCATCCGATG) were ligated into the EcoRI site to form plasmid pSV2neo-Cla. Plasmid pSV2neo-Cla was then totally digested with restriction enzymes BamHI and ClaI and the about 4.5 kb vector fragment was isolated. Plasmid pHGCEM-30 was totally digested with restriction enzyme ClaI, then partially digested with restriction enzyme BamHI and the about 12.7 kb restriction fragment, comprising the gene encoding the CEM heavy chain variable region linked to the gene encoding the human heavy chain constant region, was isolated. The about 12.7 kb ClaI/BamHI restriction fragment of plasmid pHGCEM-30 was ligated into the about 4.5 kb ClaI/BamHI vector fragment of plasmid pSV2neo-Cla to form expression vector pNCEMG1. Restriction site and function maps of plasmids pHGCEM-30 and pNCEMG1 are presented in FIGS. 7 and 8 of the accompanying drawings, respectively.

Plasmid pNCEMG1 is next treated in such a manner as to delete certain sites on the plasmid. The plasmid is first digested with restriction enzyme NotI, then treated with Klenow enzyme and self-ligated to delete the NotI site and thereby create plasmid pNCEMG1AN. This plasmid is then partially digested with restriction enzyme BamHI, treated with Klenow and self-ligated to delete two of the three BamHI sites on the plasmid and thereby create plasmid pNCEMG1ΔB2. The BamHI sites which are deleted are the sites immediately 5' to the CEM structural gene and between the human gamma 1 gene and the neomycin resistance conferring gene. The BamHI site found immediately 3' of the CEM structural gene is maintained. Plasmid pNCEMG1ΔNΔB2 is then digested with restriction enzyme SalI, treated with Klenow, then self-ligated to delete the two SalI sites which are found 5' to the human gamma 1 gene and thereby created plasmid pNCEMG1ΔNΔB2ΔS2.

Plasmid pG4G21 is then digested with restriction enzymes EcoRI and MaeIII and the approximately 421 base pair EcoRI/MaeIII restriction fragment, which comprises most of the gene encoding the 9.2.27 gamma variable region, is isolated. A BclI/EcoRI linker is then synthesized. This linker has the following sequence:

```
5'-GATCAGGGTCCG      -3'
3'-     TCCCAGGCTTAA-5'
```
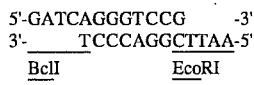

A MaeIII-BamHI linker, which contains the coding sequence for the 5 amino acids at the NH₂ terminus of the 9.2.27 gamma variable region plus a eukaryotic splice site, is then synthetized. This linker has the sequence:

```
5'-GTCACCGTCTCCTCAGGTAAG      -3'
3'-     GCAGAGGAGTCCATTCCTAG-5'
```
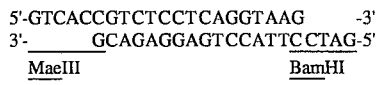

Figure 12:
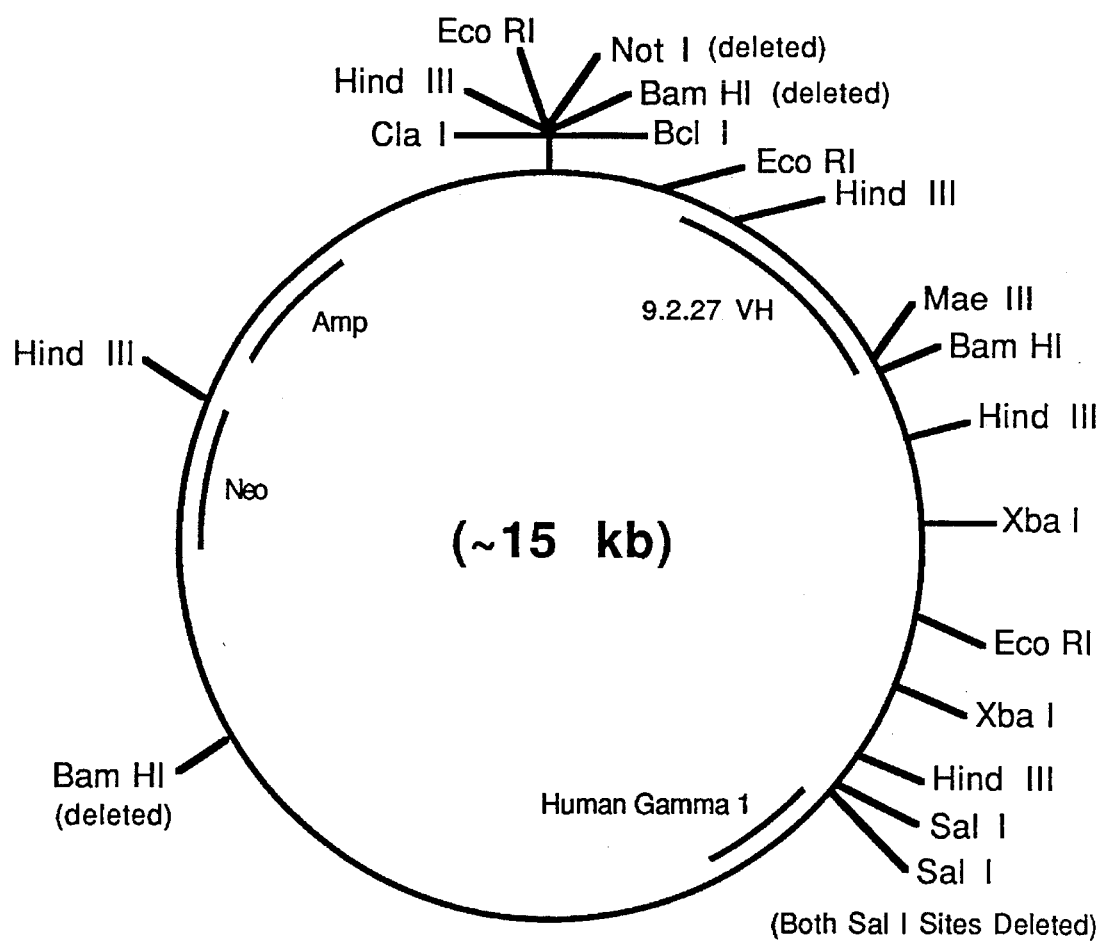
FIG. 12—The Restriction Site and Function Map of Plasmid pN9.2.27G1.

The two linkers are then ligated to the approximately 421 base pair EcoRI/MaeIII restriction fragment of plasmid p4G21. After digestion with restriction enzymes BClI and BamHI, this approximately 462 bp fragment is isolated and purified. Plasmid pNCEMG1ΔNΔB2ΔS2 is digested with restriction enzymes BclI and BamHI to remove the gene encoding the anti-CEA gamma chain variable region. The approximately 462 bp BclI/BamHI restriction fragment is then ligated into the BclI/BamHI-digested large vector fragment of plasmid pNCEMG1ΔNΔB2ΔS2 to form plasmid pN9.2.27, which comprises the gamma promoter of plasmid pNCEMG1, the gene encoding the heavy chain variable region of antibody 9.2.27, a gene encoding a human gamma chain constant region and a neomycin resistance-conferring gene. A restriction site and function map of plasmid pN9.2.27G1 is presented in FIG. 12 of the accompanying drawings.

The present DNA compounds which encode recombinant 9.2.27 immunoglobulins and derivatives are especially preferred for the construction of vectors for transformation and expression of the various antibody chains in mammalian and other eukaryotic cells. Many mammalian host cells possess the necessary cellular machinery for the recognition and proper processing of the signal peptides present on the amino-terminus of the various antibody chains embodied in the present invention. Some mammalian host cells also provide the post-translational modifications, such as glycosylation, that are observed in antibody molecules. A wide variety of vectors exist for the transformation of eukaryotic host cells, and the specific vectors exemplified below are in no way intended to limit the scope of the present invention.

The various expression vectors of the present invention can be transformed into and expressed in a variety of eukaryotic, especially mammalian, host cells. The expression vectors also comprise sequences that allow for replication in $E.\ coli$. Expression of antibodies occurs in host cells in which the particular promoter associated with the antibody's structural gene functions. Skilled artisans will understand that a variety of eukaryotic host cells can be used to express the various antibody chains of the present invention. The SP2/0-Ag14 cell line is a myeloma cell line which ordinarily does not secrete antibody. Following transfection of cell line SP2/0 with plasmids pG9.2.27K and pN9.2.27G1, the transfected cell line secretes chimeric 9.2.27 antibody into the culture fluid. Subcloning experiments, followed by conversion of the secreting cells into serum-free media, demonstrate that the chimeric antibodies could be expressed at levels up to 15 µg/ml/$10^6$ cells. While SP2/0 cells are the preferred host cells for the expression vectors of the present invention, skilled artisans recognize that a wide variety of cells may be utilized to express the bifunctional chimeric antibodies or derivatives of the present invention.

The host cells used in the invention may be transformed in a variety of ways by standard transfection procedures well known in the art. Among the standard transfection procedures which may be used are electroporation techniques, protoplast fusion and calcium-phosphate precipitation techniques. Such techniques are generally described by Toneguzzo, F. et al., *Mol. and Cell. Biol.*, 6: 703–706 (1986); Chu, G., et al., *Nucleic Acid Res.*, 15: 1311–1325 (1987); Rice, D., et al., *Proc. Natl. Acad. Sci. USA*, 79: 7862–7865 (1979) and; Oi, V., et al, *Proc. Natl. Acad. Sci. USA*, 80: 825–829 (1983).

Preferably, the recombinant expression vectors comprising the chimeric constructs of the invention are transfected sequentially into host cells. For example, the expression vector comprising the kappa chain constructs are first transfected into the host cells and transformed host cells expressing the kappa chains are selected by standard procedures known in the art. The expression vectors comprising the heavy chain gene constructs are, thereafter, transfected into the selected host cells. However, it will be recognized that both the light and heavy chain constructs can be simultaneously introduced into the host cells or introduced in inverse order. Alternatively, both the light and heavy chain gene constructs can be combined on a single expression vector, or the two DNA's could be linearized and ligated together prior to transformation into cells. Following transfection and selection, standard assays are performed for the detection of antibodies directed against CEP for the identification of transformed cells expressing the 9.2.27 chimeric antibodies of the present invention. Such assays are described in Bumol et al., (1982) *Proc. Natl. Acad. Sci. USA*, 79:1245–1249, the teaching of which is herein incorporated by reference, and Bumol et al., (1984) *J. Biol. Chem.*, 259:12733–12741, the entire disclosure of which is herein incorporated by reference.

After expression of the genes within the transfected host, the mature chimeric 9.2.27 antibodies are secreted into the supernatant. As many recombinantly produced antibodies display unwanted heterogeneity (arising from an extraneous amino acid or amino acids appearing at the C-terminus of some gamma chains), the culture fluid is generally concentrated and treated with a solution of carboxypeptidase after culture collection. The chimeric 9.2.27 antibodies can then be purified according to techniques well known in the art.

Many modifications and variations of the present illustrative DNA sequences and plasmids are possible. For example, the degeneracy of the genetic code allows for the substitution of nucleotides throughout polypeptide coding regions. Such sequences can be deduced from the now-known amino acid or DNA sequence of 9.2.27 and can be constructed by following conventional synthetic procedures. Such synthetic methods can be carried out in substantial accordance with the procedures of Itakura et al., 1977 Science 198:1056 and Crea et al., 1978, Proc. Nat. Acad. Sci. USA 75:5765. In addition, synthetic genes and linkers can be synthesized either by using a Systec 1450A DNA synthesizer (Systec Inc., 3816 Chandler Drive, Minneapolis, Minn.) or an ABS 380A DNA synthesizer (Applied Biosystems, Inc., 850 Lincoln Center Drive, Foster City, Calif. 94404). Many other DNA synthesizing instruments are known in the art and can be used to make synthetic DNA fragments. Therefore, the present invention is in no way limited to the DNA sequences and plasmids specifically exemplified.

Those skilled in the art will recognize that the expression vectors of this invention are used to transform eukaryotic host cells, such that polypeptides with various light and heavy chain structures are expressed by the host cell. If the host cell is transformed with a vector comprising a promoter that functions in the host cell and drives transcription of the such immunoglobulin structural genes, and if the host cell possesses the cellular machinery with which to process the signal peptides, mature antibodies or antibody chains are secreted by such cells. Under other expression conditions, such as when only immunoglobulin light chains are expressed by the host cell, the light chains must be isolated from the host cell.

As stated above, the vectors, methods, transformants and antibodies of the present invention will have a profound effect upon the battle against cancer. Monoclonal antibody 9.2.27 is an effective agent for the diagnosis, prognosis and treatment of human melanoma. Biochemical and immunological studies reveal that the recombinant and chimeric 9.2.27 molecules of the present invention possess the same antigen reactivity as 9.2.27 molecules derived from hybridoma cells.

The problem with using a murine antibody, however, is that said antibodies often illicit an immunological response in human subjects. This problem can be circumvented by using the chimeric antibodies of the present invention. By replacing the constant regions of 9.2.27 with constant regions of human origin, the patient's immune system will recognize the chimeric antibody as "self", and therefore create fewer anti-9.2.27 antibodies. Furthermore, the use of a human constant region will assist in the activation of complement and other cellular responses.

Skilled artisans will also recognize that the heretofore unknown amino acid and DNA sequences of 9.2.27 can be used to create novel, high or low affinity derivatives. Various portions of the antibody may be deleted or mutated to create new antibodies, or portions of one chain may be replaced with a piece of another chain. X-Ray crystallographic studies will demonstrate which amino acid residues-of the antibody appear in close proximity to epitopes of the antigen to which 9.2.27 binds. By using protein engineering techniques, 9.2.27 can be modified to provide "engineered" antibodies which will display modified affinity to the cell surface antigen in cancer patients.

The following examples further illustrate the invention disclosed herein. The examples describe the procedures for the construction of the present invention, and explanations of the procedures are provided where appropriate. The examples are offered for purposes of illustration of the present invention and are not intended to limit it in any way. While the amino acid and nucleotide sequences herein disclosed comprise the constructed components of the chimeric 9.2.27 antibody, it is understood that minor modifications to the sequences may result in variable regions which are substantially equivalent in the binding of antigen. These modifications are contemplated by the present invention provided the requisite specificities for antigen are retained.

EXAMPLE 1

Isolation of Plasmid pMLCE-10

Lyophils of *E. coli* K12 HB101/pMLCE-10 are obtained from the American Type Culture Collection, 12301 Parklawn Drive, Rockville, Md. 20852, under the accession number ATCC 67639 (deposited Mar. 1, 1988). The lyophils are decanted into tubes containing 10 ml LB medium (10 g Bacto-tryptone, 5 g Bacto-yeast extract, and 10 g NaCl per liter; pH is adjusted to 7.5) and incubated two hours at 37° C., at which time the cultures are made 50 µg/ml in ampicillin and then incubated at 37° C. overnight. Plasmid pMLCE-10 comprises the gene encoding the light chain variable region of the CEM 231.6.7 monoclonal antibody, which recognizes human carcinoembryonic antigen.

A small portion of the overnight culture is placed on LB-agar (LB medium with 15 g/l Bacto-agar) plates containing 50 µg/ml ampicillin in a manner so as to obtain a single colony isolate of *E. coli* K12 HB101/pMLCE-10. The single colony obtained was inoculated into 10 ml of LB medium containing 50 µg/ml ampicillin and incubated overnight at 37° C. with vigorous shaking. The 10 ml overnight culture was inoculated into 500 ml LB medium containing 50 µg/ml ampicillin and incubated at 37° C. with vigorous shaking until the culture reached stationary phase.

The following procedure is adapted from Maniatis et al., 1982, Molecular Cloning (Cold Spring Harbor Laboratory). The cells were harvested by centrifugation at 4000 g for 10 minutes at 4° C., and the supernatant was discarded. The cell pellet was washed in 100 ml of ice-cold STE buffer (0.1M NaCl; 10 mM Tris-HCl, pH 7.8; and 1 mM EDTA). After washing, the cell pellet was resuspended in 10 ml of Solution 1 (50 mM glucose; 25 mM Tris-HCl, pH 8.0; and 10 mM EDTA) containing 5 mg/ml lysozyme and left at room temperature for 10 minutes. Twenty ml of Solution 2 (0.2 N NaOH and 1% SDS) were then added to the lysozyme-treated cells, and the solution was gently mixed by inversion. The mixture was incubated on ice for 10 minutes.

Fifteen ml of ice-cold 5M potassium acetate, pH 4.8, were added to the lysed-cell mixture and the solution mixed by inversion. The solution was incubated on ice for 10 minutes. The 5M potassium acetate solution was prepared by adding 11.5 ml of glacial acetic acid to 28.5 ml of water and 60 ml of 5M potassium acetate; the resulting solution is 3M with respect to potassium and 5M with respect to acetate.

The lysed cell mixture was centrifuged in a Beckman SW27 (or its equivalent) at 20,000 rpm for 20 minutes at 4° C. The cell DNA and debris formed a pellet on the bottom of the tube. About 36 ml of supernatant were recovered, and 0.6 volumes of isopropanol were added, mixed, and the resulting solution left at room temperature for 15 minutes. The plasmid DNA was collected by centrifugation at 12,000 g for 30 minutes at room temperature. The supernatant was discarded, and the DNA pellet was washed with 70% ethanol at room temperature. The ethanol wash was decanted, and the pellet was dried in a vacuum desiccator. The pellet was then resuspended in 8 ml of TE buffer (10 mM Tris-HCl, pH 8.0, and 1 mM EDTA).

Eight grams of CsCl were added to the DNA solution. About 0.8 ml of a 10 mg/ml solution of ethidium bromide in water were added for each 10 ml of CsCl-DNA solution. The final density of the solution was about 1.55 g/ml, and the ethidium bromide concentraton was about 600 µg/ml. The solution was transferred to a Beckman Type 50 centrifuge tube, filled to the top with paraffin oil, sealed, and centrifuged at 45,000 rpm for 24 hours at 20° C. After centrifugation, two bands of DNA were visible in ordinary light. After removing the cap from the tube, the lower DNA band was removed by using a syringe with a #21 hypodermic needle inserted through the side of the centrifuge tube.

The ethidium bromide was removed by several extractions with water-saturated 1-butanol. The CsCl was removed by dialysis against TE buffer. After extractions with buffered phenol and then chloroform, the DNA was precipitated, washed with 70% ethanol, and dried. About 1 mg of plasmid pMLCE-10 was obtained and stored at 4° C. in TE buffer at a concentration of about 1 μg/μl. A restriction site and function map of plasmid pMLCE-10 is presented in FIG. 1 of the accompanying drawings.

EXAMPLE 2

Construction of Plasmid pHKCE-10

About 10 μl of the plasmid pMLCE-10 DNA prepared in Example 1 were mixed with 20 μl 10 X HindIII restriction buffer (500 mMNaCl; 500 mM Tris-HCl, pH 8.0; 100 mMMgCl$_2$; and 10 mMDTT), 20 μl 1 mg/ml BSA, 5 μl restriction enzyme HindIII (~50 Units, as defined by Bethesda Research Laboratories (BRL), from which all restriction enzymes used herein were obtained), and 145 μl of water, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the HindIII digestion as described above, the HindIII-digested plasmid pMLCE-10 DNA was precipitated and then resuspended in 5 μl of TE buffer.

The approximately 3.8 kb HindIII restriction fragment of plasmid pMLCE-10, which comprises the entire CEM 231.6.7 variable kappa region, was isolated by electrophoresis of the HindIII-digested plasmid pMLCE-10 DNA in a 0.75% TBE agarose gel containing 0.5 μg/ml ethidium bromide at 30V overnight. Following visualization on a UV transparent light box the approximately 3.8 kb HindIII restriction fragment was electrophoresed onto DEAE 81 (Schleicher and Schuell, Keene, N.H.) paper followed by elution in 1M NaCl and ethanol precipitation. The eluted fragment was then resuspended in 5 μl of TE buffer.

A lyophil of *E. coli* K12 HB101/pHKF-1 is obtained from the ATCC under the accession number ATCC 67637 (deposited Mar. 1, 1988). Plasmid pHKF-1, which comprises a gene encoding the human kappa constant region, was isolated from a culture of *E. coli* K12 HB101/pHKF-1 in substantial accordance with the teaching of Example 1. A restriction site and function map of plasmid pHKF-1 is presented in FIG. 2 of the accompanying drawings. One microgram of plasmid pHKF-1 was digested with restriction enzyme HindIII and the linear plasmid was isolated and purified from an agarose gel as taught above.

About one microgram (2 μl) of the approximately 3.8 kb HindIII restriction fragment of plasmid pMLCE-10 was ligated to about 600 ng (0.5 μl) of the HindIII-digested plasmid pHKF-1 in 2.5 μl of 10X ligase buffer (300 mM Tris-HCl, pH 7.6; 100 mMMgCl$_2$ and 50 mM DTT), 2.5 μl of 1 mg/ml BSA, 7 μl of 5 mMATP, 2.5 μl (about 2.5 units as defined by P-L Biochemicals) of T4 DNA ligase and 18 μl of water. The resulting ligation mixture was incubated at 12° C. overnight. The ligated DNA constituted the desired plasmid pHKCE-10.

EXAMPLE 3

Construction of *E. coli* K12 HB101/pHKCE-10

*E. coli* K12 HB101 can be obtained from the Northern Regional Research Laboratories, in Peoria, Ill., lyophylized form under the accession number NRRL B-15626 (deposited Sep. 28, 1983). The lyophils are reconstituted, single colonies of HB101 are isolated, and a 10 ml overnight culture of the HB101 cells is prepared in substantial accordance with the procedure of Example 1, except that no ampicillin is used in the growth media.

Fifty μl of the overnight culture were used to inoculate 5 ml of LB media which also contained 10 mM MgSO$_4$ and 10 mM MgCl$_2$. The culture was incubated at 37° C. overnight with vigorous shaking. The following morning, the culture was diluted to 200 ml with LB media containing 10 mMMgSO$_4$ and 10 mMMgCl$_2$. The diluted culture was incubated at 37° C. with vigorous shaking until the absorbance at 550 nm (A$_{550}$) was about 0.5, which indicated a cell density of about 1×10$^8$ cells/ml. The culture was cooled for ten minutes in an ice-water bath, and the cells were then collected by centrifugation at 4000 g for 10 minutes at 4° C. The cell pellet was resuspended in 100 ml of cold 10 mM MgSO$_4$ and then immediately re-pelleted by centrifugation. The cell pellet was resuspended in 100 ml of 30 mM CaCl$_2$ and incubated on ice for 20 minutes.

The cells were again collected by centrifugation and resuspended in 10 ml of 30 mM CaCl$_2$. A one-half ml aliquot of the cells was added to the ligated DNA prepared in Example 2; the DNA had been made 30 mM in CaCl$_2$. The cell-DNA mixture was incubated on ice for one hour, heat-shocked at 42° C. for 90 seconds, and then chilled on ice for about two minutes. The cell-DNA mixture was diluted into 10 ml of LB media in 125 ml flasks and incubated at 37° C. for one hour. One hundred μl aliquots were plated on LB-agar plates containing ampicillin and incubated at 37° C. until colonies appeared. Alternatively the DNA can be transformed into frozen, competent *E. coli* K12 HB101 cells which are commercially available from BRL, P.O. Box 6009, Gaithersburg, Md. 20877.

The colonies were individually cultured, and the plasmid DNA of the individual colonies was examined by restriction enzyme analysis and gel electrophoresis. Plasmid DNA isolation was performed on a smaller scale in accordance with the procedure of Example 1, but the CsCl gradient step was omitted until the desired *E. coli* K12 HB101/pHKCE-10 transformants were identified. A restriction site and function map of plasmid pHKCE-10 is presented in FIG. 3 of the accompanying drawings.

EXAMPLE 4

Construction of Plasmid DGCEMK

The eukaryotic expression vector containing the murine kappa variable region gene fused to the human kappa constant region gene was constructed using the vector pSV2gpt, which is publicly available from the ATCC under the accession number ATCC 37145. About one μg of plasmid pSV2gpt was digested with restriction enzyme EcoRI in substantial accordance with the teaching of Example 2, except 10X EcoRI Buffer (500 mM NaCl$_2$; 1M Tris-HCl, pH 7.5 and 50 mMMgCl$_2$) and restriction enzyme EcoRI were used. After ethanol precipitation and purification, the EcoRI ends were blunted by the addition of 10 μl of 5 mM each of the four deoxyribonucleotides dTTP, dGTP, dCTP and dATP, two units of Klenow enzyme and 5 μl of 10X Klenow Buffer (500 mM Tris-HCl, pH 7.5; 100 mMMgCl$_2$ and 10 mMDTT) in a total of 50 μl as described in *Molecular Cloning*, supra. The reaction was allowed to proceed for 30 minutes at room temperature, then the entire mixture was phenol/chloroform extracted, ethanol precipitated and resuspended in 5 μl of water.

Linkers were then added to the blunted vector. The ClaI linkers comprised the sequence, d(pCATCCGATG) and were purchased from NEB in Beverly, Mass. Alternatively, linkers can be synthesized with commercially available instruments, such as the 380A DNA Synthesizer marketed by Applied Biosystems (850 Lincoln Center Drive, Foster City, Calif. 94404), which utilizes phosphoramidite chemistry. Other procedures for synthesizing DNA are also known in the art. The conventional modified phosphotriester method of synthesizing single stranded DNA is described in Itakura et al., 1977, Science 198:1056 and in Crea et al., 1978, Proc. Nat. Acad. Sci. USA 75:5765. In addition, an especially preferred method of synthesizing DNA is disclosed in Hsiung et al., 1983, Nucleic Acid Research 11:3227 and Narang et al., 1980, Methods in Enzymology 68:90.

About 2 μg of the ClaI linkers were kinased in a mixture containing 10 μl 5X Kinase Buffer (300 mM Tris-HCl, pH 7.8; 50 mMMgCl$_2$ and 25 mM DTT), 5 μl 5 mM ATP, 24 μl H$_2$O, 0.5 μl of T4 polynucleotide Kinase (about 2.5 units as defined by P-L Biochemicals), 5 μl 1 mg/ml BSA, and 5 μl of 10 mM spermidine by incubating the mixture at 37° C. for 30 minutes. About 12.5 μl of the Kinased ClaI linkers were added to about 500 ng of the EcoRI-cut, blunted pSV2gpt vector and a ligation reaction was performed in substantial accordance with the teaching of Example 2. The sample was then electrophoresed and the vector was isolated and purified from DEAE 81 paper, then self-ligated and transformed into *E. coli* HB101 cells in accordance with the teaching of Example 3. Plasmids isolated from ampicillin resistant colonies were analyzed and those containing the proper ClaI restriction site were designated plasmid pSV2gpt-Cla.

About 1 μg of plasmid pSV2gpt-Cla was digested in substantial accordance with the teaching of Example 2, except restriction enzymes ClaI and BamHI were used, and the approximately 4.5 kb BamHI-ClaI restriction fragment was isolated from an agarose gel and purified from DEAE 81 paper. In the same manner, plasmid pHKCE-10 was digested with the same two restriction enzymes and the about 9 kb BamHI-ClaI restriction fragment was isolated and purified. This approximately 9 kb restriction fragment, which comprises the gene encoding the murine kappa variable region of antibody CEM 231.6.7 joined to the gene encoding the human kappa constant region, was ligated into the approximately 4.5 kb ClaI-BamHI fragment of vector pSV2gpt-ClaI. The ligation mixture was transformed into *E. coli* HB101 and the recombinant plasmids from ampicillin resistant colonies were tested for proper restriction sites. Those plasmids with the proper maps were designated plasmid pGCEMK. A restriction site and function map of plasmid pGCEMK is presented in FIG. 4 of the accompanying drawings.

EXAMPLE 5

Construction of plasmid pHGCEM-30

Plasmid pMHCE-30 comprises a gene encoding the murine gamma variable region of antibody CEM 231.6.7, and can be isolated from *E. coli* K12 HB101/pMHCE-30, a strain which was deposited on Mar. 1, 1988 with the ATCC and which is available under the accession number ATCC 67640. Plasmid pHG1Z comprises a gene encoding the human gamma constant region and can be isolated from *E. coli* K12 HB101/pHG1Z, a strain also deposited with the ATCC on Mar. 1, 1988, and available under the accession number ATCC 67638. Restriction site and function maps for plasmids pMHCE-30 and pHG1Z are presented in FIGS. 5 and 6 of the accompanying drawings, respectively.

The murine variable heavy chain gene was fused to the human gamma-1 gene in the following manner. About 10 μg of plasmid pMHCE-30 was digested with restriction enzyme ClaI (1 unit/μg) and then partially digested with restriction enzyme HindIII to produce an approximately 5.3 kb ClaI-HindIII restriction fragment containing the heavy chain variable gene on the major intron. Partial digests were performed by using only 0.1 unit/μg of DNA and a digestion time of 1 hour at 37° C. About 1 μg of plasmid pHG1Z containing the human gamma-1 gene was also digested with restriction enzymes ClaI and HindIII. The approximately 5.3 kb restriction fragment from plasmid pMHCE-30 was isolated from a gel and DEAE 81 in substantial accordance with the teaching of Example 2. This fragment was ligated into the ClaI-HindIII site of plasmid pHG1Z by using 500 ng of the insert and 200 ng of the digested vector DNA in a ligation mixture of 10 μl total volume, in substantial accordance with the teaching of Example 2. The recombinant plasmids resulting from transformation of *E. coli* K12 PIB101 were analyzed by restriction digestion mapping to identify plasmids containing the murine heavy chain variable region gene fused to a human gamma-1 constant region gene, which were designated plasmid pHGCEM-30. A restriction site and function map of plasmid pHGCEM-30 is presented in FIG. 7 of the accompanying drawings.

EXAMPLE 6

Construction of plasmid pNCEMG1

The chimeric Ig gene was inserted into the eukaryotic expression vector essentially as detailed in Example 4. The vector used was pSV2neo, which is publicly available from the ATCC under the accession number ATCC 37149. A ClaI site was added to this vector in substantial accordance with the teaching of Example 4, to form plasmid pSV2neo-Cla. About 1 μg of plasmid pSV2neo-Cla was digested with restriction enzymes ClaI and BamHI using 1 unit/μg of DNA. About 1 μg of plasmid pHGCEM-30 was totally digested with restriction enzyme ClaI and then partially digested with restriction enzyme BamHI (0.1 unit/μg) to obtain an approximately 12.7 kb ClaI-BamHI restriction fragment which contained the chimeric variable and gamma-1 region genes. This fragment was isolated on DEAE 81 paper and eluted in 10 μl of TE buffer. The ligation was performed using 50 ng of vector DNA, 400 ng of the approximately 12.7 kb insert DNA, 10X ligation buffer, 10 mM ATP and T4 DNA ligase at 12° C. overnight, in substantial accordance with the teaching of Example 2. *E. coli* K12 HB101 cells were transformed and restriction mapping was used to identify the recombinant plasmid designated pNCEMG1. A restriction site and function map of plasmid pNCEMG1 is presented in FIG. 8 of the accompanying drawings.

EXAMPLE 7

Construction of Plasmid pG9.2.27K

Plasmid pTZK910 comprises the gene encoding the entire 9.2.27 Kappa variable region gene inserted into plasmid pTZ18U. Plasmid pTZK910 can be isolated from *E. coli* K12 JM109/pTZK910, a strain deposit with the NRRL on Apr. 7, 1989 and available to the public under the accession number NRRL B-18478. A restriction site and function map of plasmid pTZK910 is provided in FIG. 9 of the accompanying drawings. Plasmid pTZK910 is isolated from the strain in substantial accordance with the teaching of Example 1, then the gene encoding the 9.2.27 Kappa variable region is isolated, linkers are added, and the gene is inserted into expression vector pGCEMK.

About 2 μg of plasmid pTZK910 is digested in substantial accordance with the teaching of Example 2, except restriction enzyme DdeI and 10X DdeI Buffer (1.5M NaCl; 60 mM Tris-HCl, pH 7.5; and 60 mM $MgCl_2$) are used. Next, the DdeI-digested plasmid is purified and digested using restriction enzyme BamHI and 10X BamHI Buffer (1.5M NaCl; 60 mM Tris-HCl, pH 7.9; and 60 mM$MgCl_2$). The plasmid is then electrophoresed through a gel and DEAE 81 paper is used to isolate and purify the approximately 357 bp DdeI-BamHI restriction fragment, which comprises most of the gene encoding the 9.2.27 Kappa variable region.

A set of linkers is then produced to facilitate the ligation of the DdeI-BamHI fragment of plasmid pTZK910 into the expression vector. Oligonucleotide linkers are produced by methods well known in the art and described in Example 4. A linker which has a BglII recognition site at one end and a DdeI site at the other end is first constructed with the following sequence:

The two strands are synthesized separately, then about 100 pmoles of each are mixed together in 5 μl TE buffer, heated to 70° C., then cooled to 12° C. overnight to allow the strands to self anneal.

In an analogous manner, a linker is synthesized which has a BamHI site at the 5' end and an SstII site at the 3' end. This linker contains the coding sequence for the 15 amino acids at the $NH_2$ terminus of the 9.2.27 Kappa variable region plus a eukaryotic splice site. The linker has the sequence:

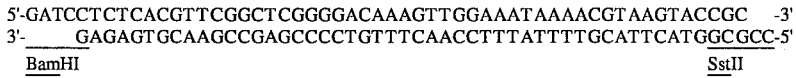

About 100 pmoles of each of the two strands are annealed together, then this BamHI-SstII linker, the annealed BglII-DdeI linker and about 0.5 μg of the DdeI-BamHI fragment of plasmid pTZK910 are ligated together in substantial accordance with the teaching of Example 4. Following the ligation, the mixture is treated with restriction enzymes BglII and SstII, then the approximately 420 base pair BglII-SstII restriction fragment, which comprises the entire coding Sequence of the 9.2.27 Kappa variable region is purified from a gel in substantial accordance with the teaching of Example 2.

About 1 μg of plasmid pGCEMK is digested with restriction enzymes BglII and SstII and the large vector fragment is gel purified. This vector comprises the gpt resistance gene and human Kappa constant region gene but not the CEM Kappa variable region gene. The approximately 420 bp BglII-SstII restriction fragment comprising the 9.2.27 Kappa variable region gene is ligated into the BglII/SstII digested plasmid pGCEMK. Following transformation and reisolation, those plasmids which display the proper restriction sites are designated plasmid pG9.2.27K. A restriction site and function map of plasmid pG9.2.27K is presented in FIG. 10 of the accompanying drawings.

EXAMPLE 8

Construction of Plasmid pN9.2.27G1

A. Construction of plasmid pNCEMG1ΔNΔB2ΔS2

To create the vector for the eukaryotic expression of the 9.2.27 chimeric gamma 1 gene, one NotI site, two BamHI sites and two SalI sites are first deleted from plasmid pNCEMG1. About 1 μg of plasmid pNCEMG1 is digested using restriction enzyme NotI and 10X NotI Buffer (1.5M NaCl; 100 mM Tris-HCl, pH 7.9; and 100 mM $MgCl_2$). After an ethanol precipitation the NotI ends are made blunt by adding 10 μl of 5 mM each of the four deoxyribonucleotides dttP, dGTP, dATP and dCTP, two units of Klenow enzyme and 5 μl of 10X Buffer (0.5M Tris-HCl, pH 7.5; 0.1M $MgCl_2$ and 10 mM DTT) in a total of 50 μl reaction volume. After 30 minutes at 37° C., the reaction is stopped by a phenol/chloroform extraction and the DNA is self-ligated and transformed into *E. coli* PIB101 cells. Those plasmids which demonstrate a deletion of the NotI site which was 5' of the structural gene are designated plasmid pNCEMG1ΔN.

In an analogous manner, plasmid pNCEMG1ΔN is partially digested with restriction enzyme BamHI, then treated with Klenow to delete two of the three BamHI sites found in the plasmid. After transformation and isolation of the random plasmids, those plasmids which demonstrate a deletion of the BamHI site 5' to the CEM structural gene and a deletion of the BamHI site between the human gamma 1 gene and the neomycin resistance-conferring gene are designated plasmid pNCEMG1ΔNΔB2. It should be noted that plasmid pNCEMG1ΔNΔB2 still maintains the BamHI site found immediately 3' of the CEM variable region gene.

Finally, the two SalI sites which are found immediately 5' of the human gamma 1 gene of plasmid pNCEMG1ΔNΔB2 are deleted. About one microgram of plasmid pNCEMG1ΔNΔB2 is digested with restriction enzyme SalI, then treated with Klenow to delete the SalI sites. After transformation and isolation of plasmids, those plasmids which demonstrate a deletion of the two SalI sites 5' to the human gamma 1 gene are designated plasmid pNCEMG1ΔNΔB2ΔS2.

B. Construction of plasmid pN9.2.27G1

Plasmid pG4G21 comprises the gene encoding the entire 9.2.27 gamma variable region inserted into plasmid pGEM4. Plasmid pG4G21 can be isolated from *E. coli* K12 DH5/pG4G21, a strain deposited with the NRRL on Apr. 7, 1989 and available to the public under the accession number NRRL B-18479. A restriction site and function map of plasmid pG4G21 is provided in FIG. 11 of the accompanying drawings. Plasmid pG4G21 is isolated from the strain in substantial accordance with the teaching of Example 1, then the gene encoding the 9.2.27 gamma variable region is isolated, linkers are added and the gene is inserted into expression vector pNCEMG1ΔNΔB2ΔS2.

About 2 μg of plasmid pG4G21 is digested in substantial accordance with the teaching of Example 2, except restriction enzyme EcoRI and 10X EcoRI Buffer are used. Next, the EcoRI-digested plasmid is purified and digested using restriction enzyme MaeIII and 10X MaeIII Buffer. The plasmid is then electrophoresed through a gel and DEAE81 paper is used to isolate and purify the approximately 421 bp EcoRI-MaeIII restriction fragment which comprises most of the gene encoding the 9.2.27 gamma variable region.

A set of linkers is then produced to facilitate the ligation of the EcoRI/MaeIII fragment of plasmid pG4G21 into the expression vector. A linker which has an BclI site at one end and an EcoRI site at the other end is synthesized, annealed and ligated to the EcoRI/MaeIII restriction fragment in substantial accordance with the teaching of Example 7. The linker has the sequence:

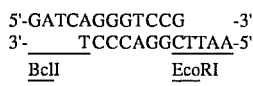

In an analogous manner, a linker is synthesized which has a MaeIII site at the 5' end and a BamHI site at the 3' end. This linker contains the coding sequence for the 5 amino acids at the $NH_2$ terminus of the 9.2.27 gamma variable region plus a eukaryotic splice site. The linker has the sequence:

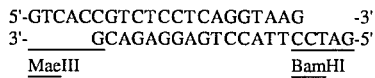

This linker is annealed, then this MaeIII-BamHI linker, the annealed BclI-EcoRI linker and about 0.5 μg of the EcoRI-MaeIII restriction fragment of plasmid pG4G21 are ligated together in substantial accordance with the teaching of Example 4. Following the ligation, the mixture is treated with restriction enzymes BclI and BamHI, then the approximately 462 base pair BclI-BamHI restriction fragment is purified from a gel in substantial accordance with the teaching of Example 2. This restriction fragment comprises the entire coding sequence of the 9.2.27 gamma variable region.

About 1 μg of plasmid pNCEMG1ΔNΔB2ΔS2 is digested with restriction enzymes BclI and BamHI and the large vector fragment is gel purified. This vector comprises the neomycin resistance-conferring gene and the human gamma 1 constant region gene but not the CEM gamma variable region gene. The approximately 462 base pair BClI-BamHI restriction fragment comprising the 9.2.27 gamma variable region gene is ligated into the BclI/BamHI-digested plasmid pNCEMG1ΔNΔB2ΔS2. Following transformation and reisolation, those plasmids which display the proper restriction sites are designated plasmid pN9.2.27G1. A restriction site and function map of plasmid pN9.2.27G1 is presented in FIG. 12 of the accompanying drawings.

EXAMPLE 9

Expression of Chimeric 9.2.27 Antibodies in Eukaryotic Cells

A. Transfection of Chimeric Light Chain Gene with the Chimeric Construct pG9.2.27K The light chain immunoglobulin plasmid used for transfection is pG9.2.27, as described in Example 7 above. The pG9.2.27 plasmid, containing the chimeric variable light ($V_K$) 9.2.27 gene fused to the human kappa gene, is first transfected into SP2/0 hybridoma cells by the electroporation techniques essentially as described by Toneguzzo et al., (1986) *Molecular and Cellular Biology* 6:703 and Chu et al., (1987) *Nucleic Acids Research* 15:1311. The host SP2/0-Ag14 hybridoma cells are the recipients of the chimeric genes. The SP2/0-Ag14 hybridoma cells are publicly available from the ATCC under the accession number ATCC CRL 1581. The SP2/0-Ag14 cells are grown in media containing 5% FCS and maintained in a log phase of growth for the three days preceeding electroporation. Twenty μg of the plasmid vector pG9.2.27 are linearized using the restriction enzyme PvuI (1 u/μg) and the PVuI Reaction Buffer (Gibco-BRL, Gaithersburg, Md.). At the time of transfection the SP2/0 cells are collected by centrifugation in an IEC clinical centrifuge—800 rpm 10' room temperature. Cells are then washed 3x in Hanks Buffered Saline Solution (Gibco Laboratories, Grand Island, N.Y.) with 6 mM Dextrose and resuspended at a final concentration of $3.0 \times 10^7$ cells/ml. 0.3 mls of cells are aliquoted into cuvettes at a density of $1 \times 10^7/0.3$ ml and the linearized DNA is added. The mixture is maintained on ice 10 minutes. Electroporation is done using the 0.8 mm gap electrode (P/N 472) and the BTX 100 Transfector (BTX, Inc. San Diego, Calif.). Conditions are 3 pulses, 100 μ seconds each at 300 volts. The electroporated cells are then resuspended in medium at a density of $2 \times 10^5$/ml (in T75 flasks) for 72 hours. (37° C. 5% $CO_2$). Cells are then plated in the appropriate antibiotic at a density of $5 \times 10^4$/ml in 24 well plates; SP2/0 cells containing pG9.2.27 are plated in HMAX 1.0 Media (50 ng/ml Hypoxanthine, 250 ng/ml Mycophenolic Acid and 50 μg/ml Xanthine), available from Sigma, St. Louis, Mo., at 1 μg/ml. Two hundred μl of supernatant is collected from each well which contain HMAX resistant colonies. This supernatant is then assayed for the presence of a human kappa constant region gene which would indicate expression of the chimeric immunoglobulin genes of pG9.2.27.

B. Identification of SP2/0 Cells Secreting Chimeric 9.2.27

Transfected SP2/0 cells expressing the chimeric CEM-human kappa genes are identified by a standard enzyme-linked immunosorbent assay (ELISA), as described by Engvall, E. and Perlmann, P., *Immunochemistry,* 8:871–874 (1971), for human kappa.

The purpose of this assay is to identify those cells secreting the chimeric kappa chain polypeptide coded for by the pG9.2.27 plasmid vector which is constructed from murine variable regions isolated from the murine hybridoma 9.2.27 and fused to the human kappa 1 gene. A 5 μg/ml solution of goat anti-human kappa chain (Tago #4106) in 10 mM sodium phosphate pH 7–8 is prepared. Each well of a 96 well plate is coated with 50 μl of this solution. The plates are then incubated overnight at 37° C. Plates are then rinsed thoroughly in $H_2O$ and PBS+0.1% Tween (w/v). Fifty μl of the supernatant fractions are added to each well, and incubated for 2 hours at room temperature. Plates are again rinsed as detailed above. A goat anti-human kappa chain alkaline phosphatase conjugate (Tago #2496) is diluted 1:1000 in the same medium as the supernatant material. 100

μl are added per well and allowed to incubate for 1 hour at room temperature. Plates are rinsed as above. The alkaline phosphatase substrate is prepared as per package instruction, one tablet per 3 ml of distilled $H_2O$ and 150 μl of this substrate is added to each well and allowed to incubate 30 minutes at 37° C. The reaction is quenched with 50 μl of 300 mM EDTA and then the absorbance is read at 405 nM. Those supernatants showing the highest levels of kappa expression are identified and the cells from the corresponding wells are pooled and expanded for introduction of the chimeric construct pN9.2.27G1.

C. Transfection of Chimeric Kappa Producing Cells with the Heavy Chain Chimeric Construct pN9.2.27

The heavy chain immunoglobulin plasmids used for transfection into SP2/0 cells was pN9.2.27, derived from constructs as detailed in Example 8. The populations of cells expressing the chimeric 9.2.27-human kappa genes which are pooled are next electroporated with the plasmid constructs containing the chimeric 9.2.27 heavy chain genes. As for the kappa gene electroporation the SP2/0 chimeric dappa producing cells (SP2/0-K) are maintained at log phase of growth for the three days preceeding the electroporation. Twenty micrograms of the plasmid DNA pN9.2.27G1 is linearized with the enzyme Pvu I in PvuI Reaction Buffer. Cells are collected, washed and resuspended at a density of $3 \times 10^7$ cells/ml as detailed in Example 9A. The DNA is added and the mixture held on ice for 10 minutes preceeding the electroporation. Conditions used are 1 pulse at 5 m seconds, 250 volts. Cells are plated at $2.5 \times 10^5$/ml in mammalian tissue culture media, such as HH2 (or any other media such as DMEM or RPMI) plus 5% FCS plus HMAX 1.0 for 72 hours at 37° C., 5% $CO_2$. Next, these cells are plated at $5 \times 10^4$/ml in 24 well plates in medium containing HMAX 1.0 and G418 antibiotic (Geneticin, Gibco-BRL, Gaithersburg, Md.) at an active concentration of 500 μg/ml. Selection is maintained for 14 days at which time those wells with HMAX/G418 resistant colonies are identified for further analysis.

It will be apparent to those skilled in the art that modifications and changes to the invention will be possible without departing from the spirit and scope of the invention. It is intended that the following claims be interpreted to embrace all such modifications and changes.

Plasmid Deposits

Under the provisions of the Budapest Treaty on the International Recognition of the Deposit of Microorganisms for Purposes of Patent Procedures, the following cultures have been deposited with the permanent culture collection of the American Type Culture Collection (ATCC) in Rockville, Md., 20852:

| Deposited Material | Date of Deposit | Accession Number |
| --- | --- | --- |
| E. coli K 12 HB101/pMLCE-10 | March 1, 1988 | ATCC 67639 |
| E. coli K 12 HB101/pHKF-1 | March 1, 1988 | ATCC 67637 |
| E. coli K 12 HB101/pMHCE-30 | March 1, 1988 | ATCC 67640 |
| E. coli K 12 HB101/pHG1Z | March 1, 1988 | ATCC 67638 |

Under the provisions of the Budapest Treaty on the International Recognition of the Deposit of Microorganisms for Purposes of Patent Procedures the following cultures have been deposited with the permanent culture collection of the Northern Regional Research Center (NRRL), Agricultural Research Service, U.S. Department of Agriculture, 1815 N. University Street, Peoria, Ill., 61604:

| Deposited Material | Date of Deposit | Accession Number |
| --- | --- | --- |
| E. coli K12 HB101 | September 30, 1983 | NRRL B-15626 |
| E. coli K12 JM109/pTZK910 | May 5, 1989 | NRRL B-18478 |
| E. coli K12 DH5/pG4G21 | May 5, 1989 | NRRL B-18479 |

We claim:

1. A recombinant DNA compound that comprises a DNA sequence encoding the light chain variable region of a chimeric monoclonal antibody, the DNA sequence coding for an amino acid sequence comprising:

```
Asn—Ile—Val—Leu—Thr—Gln—Ser—Pro—Ala—Ser
Leu—Ala—Val—Ser—Leu—Gly—Gln—Arg—Ala—Thr
Ile—Ser—Cys—Arg—Ala—Ser—Glu—Ser—Val—Asp
Ser—Tyr—Gly—Asn—Ser—Phe—Met—His—Trp—Tyr
Gln—Gln—Lys—Pro—Gly—Gln—Pro—Pro—Lys—Leu
Leu—Ile—Tyr—Leu—Ala—Ser—Asn—Leu—Glu—Ser
Gly—Val—Pro—Ala—Arg—Phe—Ser—Gly—Ser—Gly
Ser—Arg—Thr—Asp—Phe—Thr—Leu—Thr—Ile—Asp
Pro—Val—Glu—Ala—Asp—Asp—Ala—Ala—Thr—Tyr
Tyr—Cys—Gln—Gln—Asn—Asn—Glu—Asp—Pro—Leu
Thr—Phe—Gly—Ser—Gly—Thr—Lys—Leu—Glu—Ile
Lys—Arg.
```

2. The recombinant DNA compound of claim 1 wherein the coding strand comprises:

```
AAC—ATT—GTG—CTG—ACC—CAA—TCT—CCA—GCT—TCT
TTC—GCT—GTG—TCT—CTA—GGG—CAG—AGG—GCC—ACC
ATA—TCC—TGC—AGA—GCC—AGT—GAA—AGT—GTT—GAT
AGT—TAT—GGC—AAT—AGT—TTT—ATG—CAC—TGG—TAC
CAG—GAG—AAA—CCA—GGA—CAG—CCA—CCC—AAA—CTC
CTC—ATC—TAT—CTT—GCA—TCC—AAC—CTA—GAA—TCT
GGG—GTC—CCT—GCC—AGG—TTC—AGT—GGC—AGT—GGA
TCT—AGG—ACA—GAC—TTC—ACC—CTC—ACC—ATT—GAT
CCT—GTG—GAG—GCT—GAT—GAT—GCT—GCA—ACC—TAT
TAC—TGT—CAA—CAA—AAT—AAT—GAG—GAT—CCT—CTC
ACG—TTC—GGC—TCG—GGG—ACA—AAG—TTG—GAA—ATA
AAA—CGG.
```

3. The recombinant DNA compound of claim 2 wherein the DNA coding sequence is derived from a murine hybridoma.

4. The recombinant DNA compound of claim 3 wherein the murine hybridoma is 9.2.27.

5. The recombinant DNA compound of claim 1 that further comprises a second DNA sequence which encodes the light chain constant region of the chimeric monoclonal antibody.

6. The recombinant DNA compound of claim 5 wherein the second DNA sequence is derived from a human lymphocyte.

7. The recombinant DNA compound of claim 1 wherein the DNA sequence further comprises a DNA sequence encoding aeukaryotic signal peptide.

8. The recombinant DNA compound of claim 7 wherein the DNA sequence encoding a leader peptide encodes a leader peptide with an amino acid sequence comprising:

Met—Glu—Thr—Asp—Thr—Leu—Leu—Leu—Trp—Val
Leu—Leu—Leu—Trp—Val—Pro—Gly—Ser—Thr—Gly.

9. The recombinant DNA compound of claim 8 wherein the DNA encoding a leader peptide comprises:

ATG—GAG—ACA—GAC—ACA—CTC—CTG—CTA—TGG—GTG
CTG—CTG—CTC—TGG—GTT—CCA—GGT—TCC—ACA—GGT.

10. A recombinant DNA vector that comprises the DNA compound of claim 9 wherein the DNA sequence is derived from a murine hybridoma.

11. The recombinant DNA vector of claim 10, wherein the DNA sequence is derived from murine hybridoma 9.2.27.

12. The recombinant DNA vector of claim 11 that is plasmid pTZK910.

13. The recombinant DNA compound of claim 9 that further comprises a second DNA sequence which encodes the light chain constant region of the chimeric monoclonal antibody.

14. The recombinant DNA compound of claim 13 wherein the second DNA sequence is derived from a human lymphocyte.

15. A recombinant DNA vector that comprises the DNA compound of claim 14.

16. The recombinant DNA vector of claim 15 that is plasmid pG9.2.27K.

17. A recombinant DNA compound that comprises a DNA sequence encoding the heavy chain variable region of a chimeric monoclonal antibody, the first DNA sequence coding for an amino acid sequence comprising:

Gln—Val—Gln—Leu—Gln—Gln—Ser—Gly—Pro—Glu
Leu—Val—Lys—Pro—Gly—Ala—Ser—Val—Lys—Ile
Ser—Cys—Lys—Ala—Ser—Gly—Tyr—Ala—Phe—Ser
Arg—Ser—Trp—Met—Asn—Trp—Val—Lys—Gln—Arg
Pro—Gly—Gln—Gly—Leu—Glu—Trp—Ile—Gly—Arg
Ile—Tyr—Pro—Gly—Asp—Gly—Asp—Thr—Asn—Tyr
Asn—Gly—Lys—Phe—Lys—Gly—Lys—Ala—Thr—Leu
Thr—Ala—Asp—Lys—Ser—Ser—Ser—Thr—Ala—Tyr
Met—Gln—Val—Ser—Ser—Leu—Thr—Ser—Val—Asp
Ser—Ala—Val—Tyr—Phe—Cys—Ala—Arg—Gly—Asn
Thr—Val—Val—Val—Pro—Tyr—Thr—Met—Asp—Tyr
Trp—Gly—Gln—Gly—Thr—Ser—Val—Thr—Val—Ser
Ser.

18. The recombinant DNA compound of claim 17 wherein the coding strand comprises:

CAG—GTC—CAG—CTG—CAG—CAG—TCT—GGA—CCT—GAG
CTG—GTG—AAG—CCT—GGG—GCC—TCA—GTG—AAG—ATT
TCC—TGC—AAA—GCT—TCT—GGC—TAC—GCA—TTC—AGT
AGG—TCT—TGG—ATG—AAC—TGG—GTG—AAG—CAG—AGG
CCT—GGA—CAG—GGT—CTT—GAG—TGG—ATT—GGA—CGG
ATT—TAT—CCT—GGA—GAT—GGA—GAT—ACT—AAC—TAC
AAT—GGG—AAG—TTC—AAG—GGC—AAG—GCC—ACA—CTG
ACT—GCA—GAC—AAA—TCC—TCC—AGC—ACA—GCC—TAC
ATG—CAG—GTC—AGC—AGC—CTG—ACC—TCT—GTG—GAC
TCT—GCG—GTC—TAT—TTC—TGT—GCA—AGA—GGG—AAT
ACG—GTA—GTA—GTT—CCC—TAT—ACT—ATG—GAC—TAC
TGG—GGT—CAA—GGA—ACC—TCA—GTC—ACC—GTC—TCC
TCA.

19. The recombinant DNA compound of claim 18 wherein the DNA coding sequence is derived from a murine hybridoma.

20. The recombinant DNA compound of claim 19 wherein the murine hybridoma is 9.2.27.

21. The recombinant DNA compound of claim 17 that further comprises a second DNA sequence which encodes the heavy chain constant region of the chimeric monoclonal antibody.

22. The recombinant DNA compound of claim 21 wherein the second DNA sequence is derived from a human lymphocyte.

23. The recombinant DNA compound of claim 17 wherein the DNA sequence further comprises a second DNA sequence encoding a eukaryotic signal peptide.

24. The recombinant DNA compound of claim 23 wherein the DNA sequence encoding a leader peptide encodes a leader peptide with an amino acid sequence comprising:

Met—Gly—Trp—Ser—Arg—Ile—Phe—Leu—Phe—Leu
Leu—Ser—Ile—Thr—Ala—Gly—Val—His—Cys.

25. The recombinant DNA compound of claim 24 wherein the DNA encoding a leader peptide comprises:

```
ATG—GGA—TGG—AGC—CGG—ATC—TTT—CTC—TTC—CTC
CTG—TCA—ATA—ACT—GCA—GGT—GTC—CAT—TGC.
```

26. A recombinant DNA vector that comprises a DNA sequence derived from a murine hybridoma and encoding the heavy chain variable region of a chimeric monoclonal antibody as claimed in claim 17 which further comprises a leader peptide comprising:

```
ATG—GGA—TTG—AGC—CGG—ATC—TTT—CTC—TTC—CTC—
CTG—TCA—ATA—ACT—GCA—GGT—GTC—CAT—TGC
```

27. The recombinant DNA vector of claim 26, wherein the DNA sequence encoding the heavy chain variable region of a chimeric monoclonal antibody is derived from murine hybridoma 9.2.27.

28. The recombinant DNA vector of claim 27 that is plasmid pG4G21.

29. The recombinant DNA compound of claim 25 that further comprises a second DNA sequence which encodes the heavy chain constant region of the chimeric monoclonal antibody.

30. The recombinant DNA compound of claim 29 wherein the second DNA sequence is derived from a human lymphocyte.

31. A recombinant DNA vector that comprises the DNA compound of claim 30.

32. The recombinant DNA vector of claim 31 that is plasmid pN9.2.27G1.

33. A transformed eukaryotic host cell capable of expression of a chimeric monoclonal antibody comprising at least one DNA vector which comprises a DNA sequence encoding for the light chain of the chimeric antibody, and transcriptional and translational DNA sequences positioned in relation to the light chain-encoding DNA sequence to direct expression of the light chain, wherein the DNA strand sequence encoding for the light chain variable region comprises:

```
AAC—ATT—GTG—CTG—ACC—CAA—TCT—CCA—GCT—TCT
TTC—GCT—GTG—TCT—CTA—GGG—CAG—AGG—GCC—ACC
ATA—TCC—TGC—AGA—GCC—AGT—GAA—AGT—GTT—GAT
AGT—TAT—GGC—AAT—AGT—TTT—ATG—CAC—TGG—TAC
CAG—GAG—AAA—CCA—GGA—CAG—CCA—CCC—AAA—CTC
CTC—ATC—TAT—CTT—GCA—TCC—AAC—CTA—GAA—TCT
GGG—GTC—CCT—GCC—AGG—TTC—AGT—GGC—AGT—GGA
TCT—AGG—ACA—GAC—TTC—ACC—CTC—ACC—ATT—GAT
```

```
-continued
CCT—GTG—GAG—GCT—GAT—GAT—GCT—GCA—ACC—TAT
TAC—TGT—CAA—CAA—AAT—AAT—GAG—GAT—CCT—CTC
```

```
-continued
ACG—TTC—GGC—TCG—GGG—ACA—AAG—TTG—GAA—ATA
AAA—CGG.
```

34. The transformed eukaryotic host cell according to claim 33 wherein a second DNA vector comprises, or the first DNA construct further comprises, a DNA strand sequence encoding for the heavy chain of the chimeric antibody, and transcriptional and translational DNA sequences positioned in relation to the heavy chain-encoding DNA strand sequence to direct expression of the heavy chain, wherein the DNA sequence encoding for the heavy chain variable region comprises:

```
CAG—GTC—CAG—CTG—CAG—CAG—TCT—GGA—CCT—GAG
CTG—GTG—AAG—CCT—GGG—GCC—TCA—GTG—AAG—ATT
TCC—TGC—AAA—GCT—TCT—GGC—TAC—GCA—TTC—AGT
AGG—TCT—TGG—ATG—AAC—TGG—GTG—AAG—CAG—AGG
CCT—GGA—CAG—GGT—CTT—GAG—TGG—ATT—GGA—CGG
ATT—TAT—CCT—GGA—GAT—GGA—GAT—ACT—AAC—TAC
AAT—GGG—AAG—TTC—AAG—GGC—AAG—GCC—ACA—CTG
ACT—GCA—GAC—AAA—TCC—TCC—AGC—ACA—GCC—TAC
ATG—CAG—GTC—AGC—AGC—CTG—ACC—TCT—GTG—GAC
TCT—GCG—GTC—TAT—TTC—TGT—GCA—AGA—GGG—AAT
ACG—GTA—GTA—GTT—CCC—TAT—ACT—ATG—GAC—TAC
TGG—GGT—CAA—GGA—ACC—TCA—GTC—ACC—GTC—TCC
TCA.
```

35. The transformed eukaryotic host cell of claim 34 wherein the first DNA vector encodes the light chain of the chimeric monoclonal antibody and the second DNA vector encodes the heavy chain of the chimeric monoclonal antibody.

36. The transformed eukaryotic host cell of claim 35 that is SP2/0/pG9.2.27K/pN9.2.27G1.

* * * * *

UNITED STATES PATENT AND TRADEMARK OFFICE
CERTIFICATE OF CORRECTION

PATENT NO. : 5,580,774

DATED : December 3, 1996

INVENTOR(S) : Beavers, et al.

It is certified that error appears in the above-identified patent and that said Letters Patent is hereby corrected as shown below:

Column 7, Line 9, "EcpRI" should read --EcoRI--

Signed and Sealed this

Twelfth Day of May, 1998

Attest:

BRUCE LEHMAN

Attesting Officer

Commissioner of Patents and Trademarks